US010386318B2

(12) United States Patent
Hay et al.

(10) Patent No.: US 10,386,318 B2
(45) Date of Patent: Aug. 20, 2019

(54) ROLLER CONE RESISTIVITY SENSOR

(71) Applicant: Halliburton Energy Services, Inc., Houston, TX (US)

(72) Inventors: Richard Thomas Hay, Spring, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 183 days.

(21) Appl. No.: 15/531,344

(22) PCT Filed: Dec. 31, 2014

(86) PCT No.: PCT/US2014/073039
§ 371 (c)(1),
(2) Date: May 26, 2017

(87) PCT Pub. No.: WO2016/108903
PCT Pub. Date: Jul. 7, 2016

(65) Prior Publication Data
US 2017/0328850 A1 Nov. 16, 2017

(51) Int. Cl.
*E21B 10/08* (2006.01)
*G01N 27/06* (2006.01)
(Continued)

(52) U.S. Cl.
CPC .............. *G01N 27/06* (2013.01); *E21B 10/08* (2013.01); *E21B 10/62* (2013.01); *E21B 47/082* (2013.01);
(Continued)

(58) Field of Classification Search
CPC ........ E21B 10/08; E21B 10/62; E21B 47/082; E21B 47/0905; E21B 47/122; E21B 49/005; E21B 12/00; G01N 27/06
See application file for complete search history.

(56) References Cited

U.S. PATENT DOCUMENTS 4,785,894 A 11/1988 Davis, Jr. et al.
5,168,942 A 12/1992 Wydrinski
(Continued)

FOREIGN PATENT DOCUMENTS

CN 1042214 A 5/1990
CN 1064913 A 9/1992
(Continued)

OTHER PUBLICATIONS

International Search Report and Written Opinion issued in related PCT Application No. PCT/US2014/073039 dated Sep. 2015, 14 pages.
(Continued)

*Primary Examiner* — Yong-Suk Ro
(74) *Attorney, Agent, or Firm* — Jason Sedano; Baker Botts L.L.P.

(57) ABSTRACT

A drilling system includes a roller cone drill bit having a roller cone and at least one antenna loop disposed in the roller cone for detecting magnetic or electromagnetic waves indicative of a target, a resistivity, or a boundary of the subterranean formation, man-made structure, or object. The drilling system may utilize the antenna loop to determine resistivity measurements of a subterranean formation through which the drill bit is being drilled. The location of the antenna in the roller cone may enable increased look-ahead and look-around measurements. In addition, the location of the antenna in the roller cone may facilitate anisotropic resistivity measurements to aid in steering the drill string into a desired portion of the subterranean formation.

20 Claims, 17 Drawing Sheets

(51) Int. Cl.
    *E21B 10/62*     (2006.01)
    *E21B 47/08*     (2012.01)
    *E21B 47/09*     (2012.01)
    *E21B 47/12*     (2012.01)
    *E21B 49/00*     (2006.01)
    *E21B 12/00*     (2006.01)

(52) U.S. Cl.
    CPC ........ *E21B 47/0905* (2013.01); *E21B 47/122* (2013.01); *E21B 49/005* (2013.01); *E21B 12/00* (2013.01)

(56) References Cited

U.S. PATENT DOCUMENTS

| | | |
|---|---|---|
| 5,720,355 A | 2/1998 | Lamine et al. |
| 5,901,797 A | 5/1999 | Hansen et al. |
| 6,057,784 A | 5/2000 | Schaaf et al. |
| 6,167,833 B1 | 1/2001 | Caraway et al. |
| 6,353,321 B1 | 3/2002 | Bittar |
| 6,480,118 B1 | 11/2002 | Rao |
| 6,698,536 B2 | 3/2004 | Moran et al. |
| 6,798,208 B2 | 9/2004 | Omeragic |
| 6,814,162 B2 | 11/2004 | Moran et al. |
| 6,819,112 B2 | 11/2004 | Gianzero et al. |
| 6,850,068 B2 | 2/2005 | Chemali et al. |
| 6,998,844 B2 | 2/2006 | Omeragic et al. |
| 7,066,280 B2 | 6/2006 | Sullivan et al. |
| 7,554,329 B2 | 6/2009 | Gorek et al. |
| 7,861,801 B2 | 1/2011 | Alberty |
| 7,948,238 B2 | 5/2011 | Bittar |
| 8,207,738 B2 | 6/2012 | Wang |
| 8,274,289 B2 | 9/2012 | Bittar et al. |
| 8,432,167 B2 | 4/2013 | Reiderman |
| 8,499,830 B2 | 8/2013 | Alberty |
| 8,528,661 B2 | 9/2013 | Patel et al. |
| 8,570,045 B2 | 10/2013 | Tchakarov et al. |
| 8,581,592 B2 | 11/2013 | Bittar et al. |
| 2005/0041526 A1 | 2/2005 | Esmersoy et al. |
| 2005/0230149 A1 | 10/2005 | Boucher et al. |
| 2011/0315444 A1 | 12/2011 | Trinh et al. |
| 2012/0024600 A1 | 2/2012 | Bittar et al. |
| 2012/0103690 A1 | 5/2012 | Patel et al. |
| 2013/0105224 A1 | 5/2013 | Donderici et al. |
| 2014/0060820 A1 | 3/2014 | Bittar et al. |
| 2014/0224539 A1 | 8/2014 | Kumar et al. |
| 2017/0321536 A1* | 11/2017 | Hay ................ E21B 47/024 |

FOREIGN PATENT DOCUMENTS

| | | |
|---|---|---|
| WO | 2010/045171 A2 | 4/2010 |
| WO | 2013/070200 A1 | 5/2013 |

OTHER PUBLICATIONS

International Preliminary Report on Patentability issued in related Application No. PCT/US2014/073039, dated Jul. 13, 2017 (13 pages).

Office Action and Search Report issued in related Chinese Patent Application No. 201480082800.0 dated Jul. 3, 2018, 8 pages (no translation.).

Examination Report No. 2 issued in related Australian Patent Application No. 2014415575 dated Jul. 19, 2018, 6 pages.

* cited by examiner

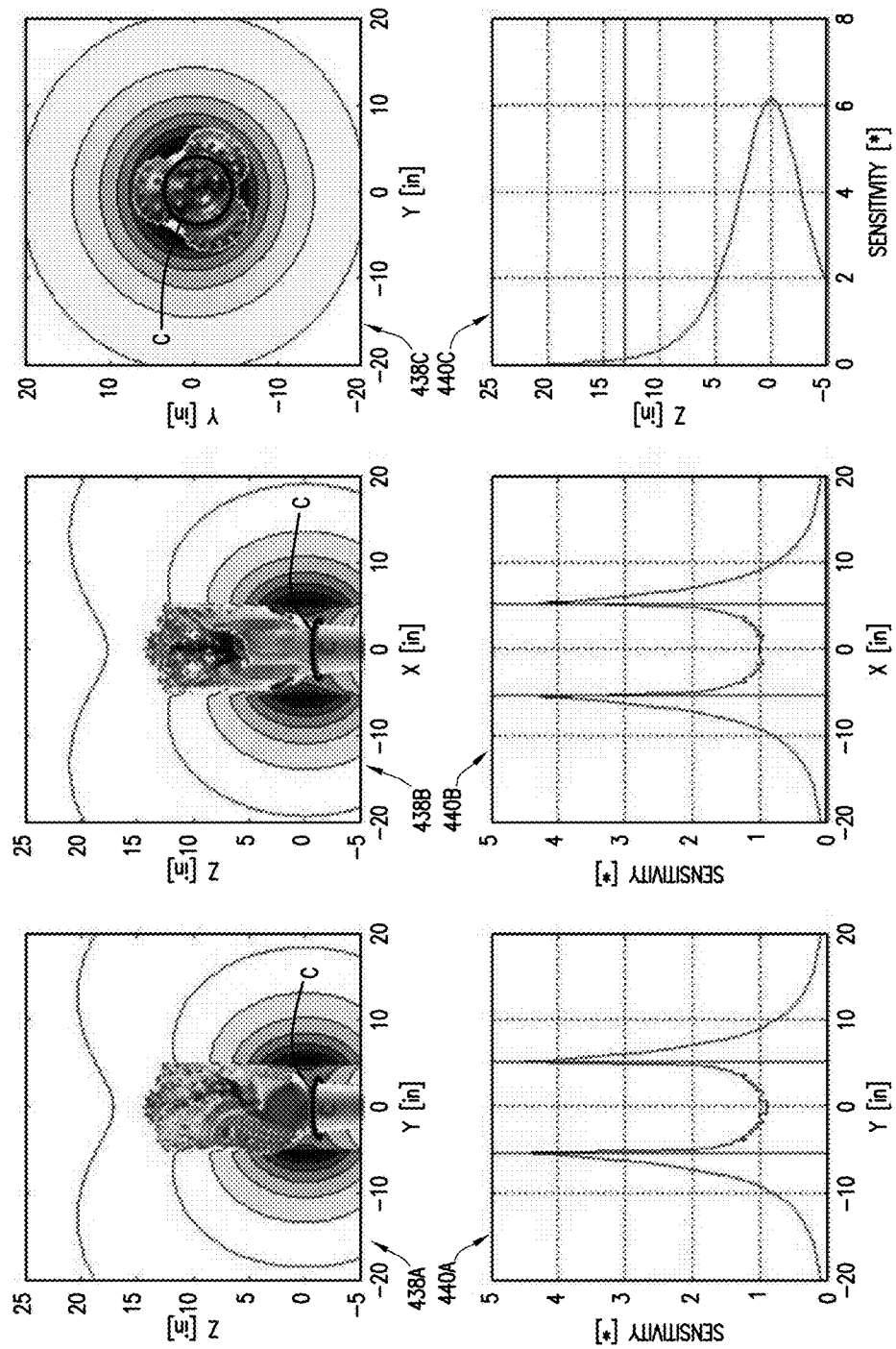

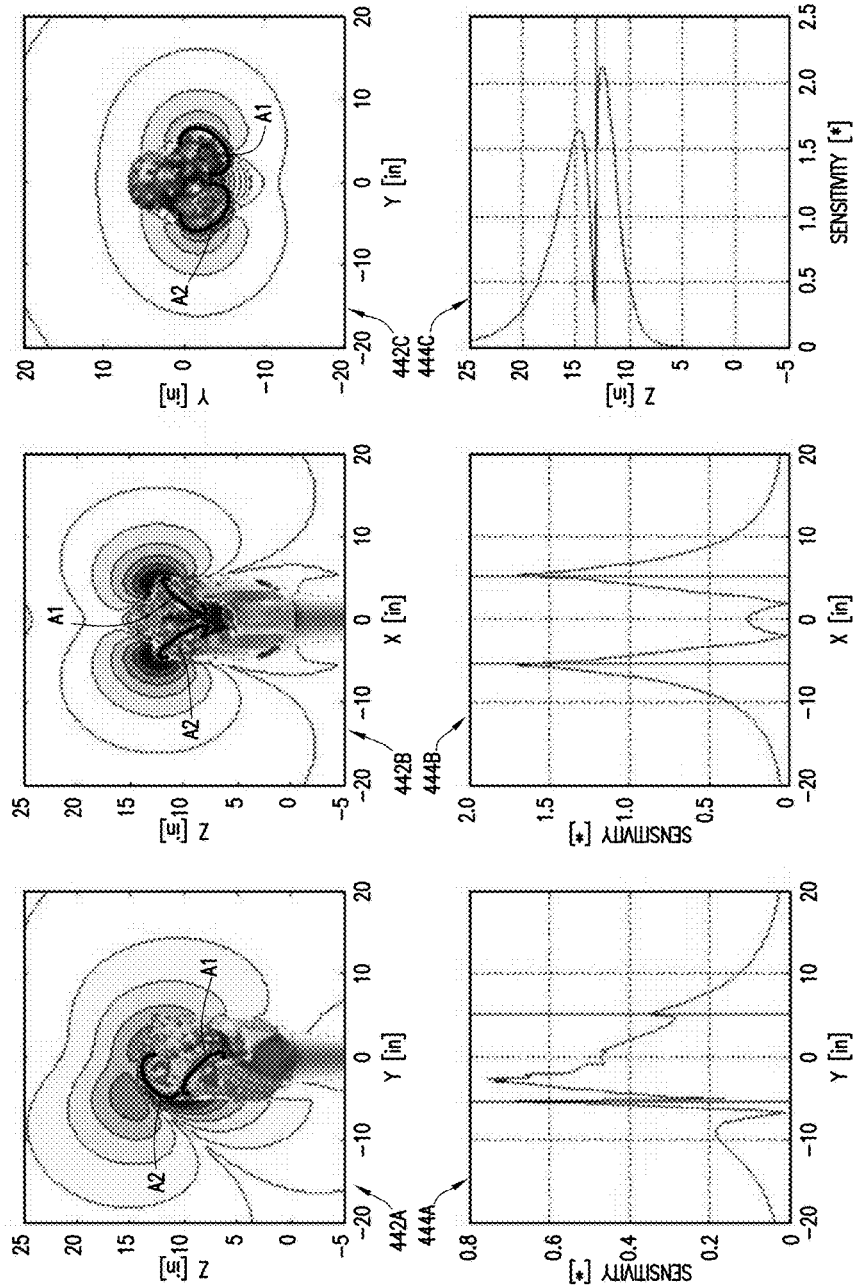

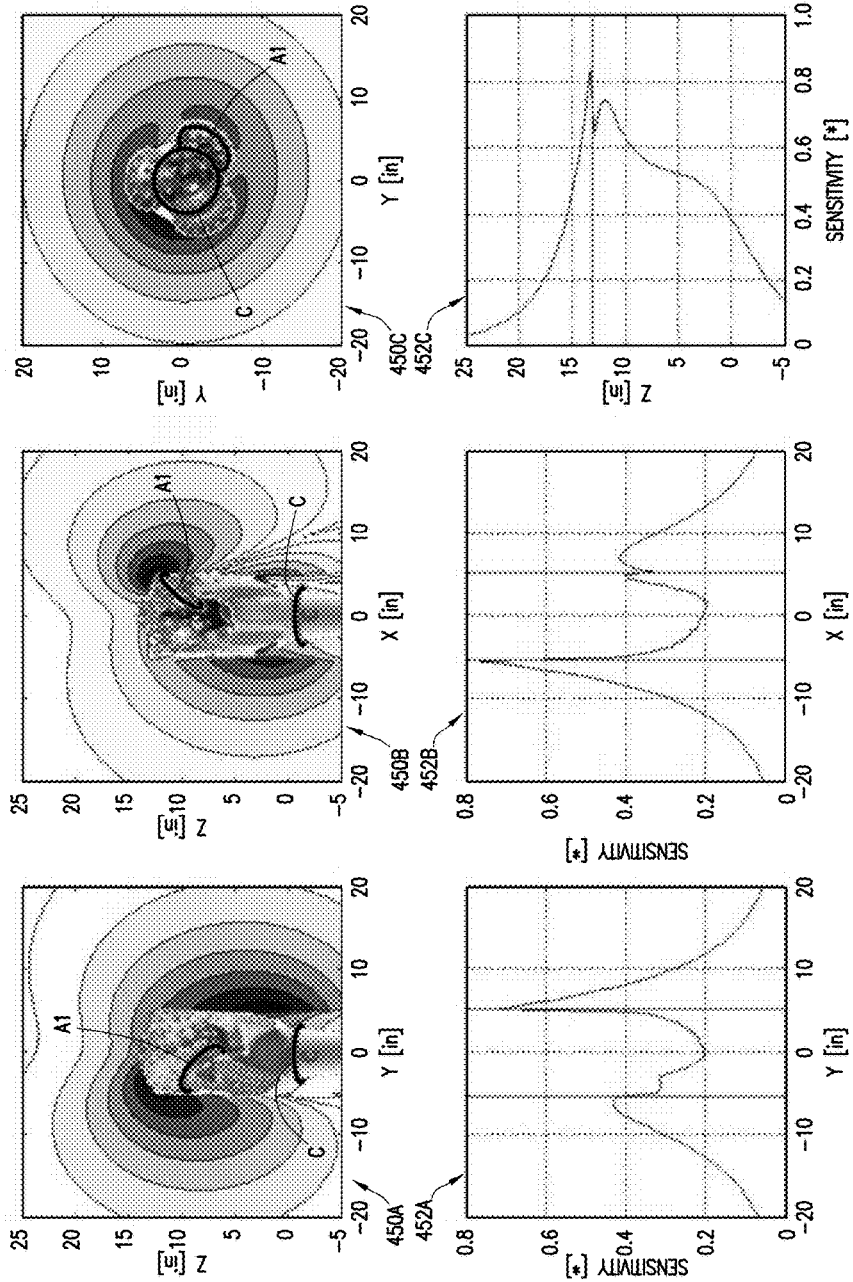

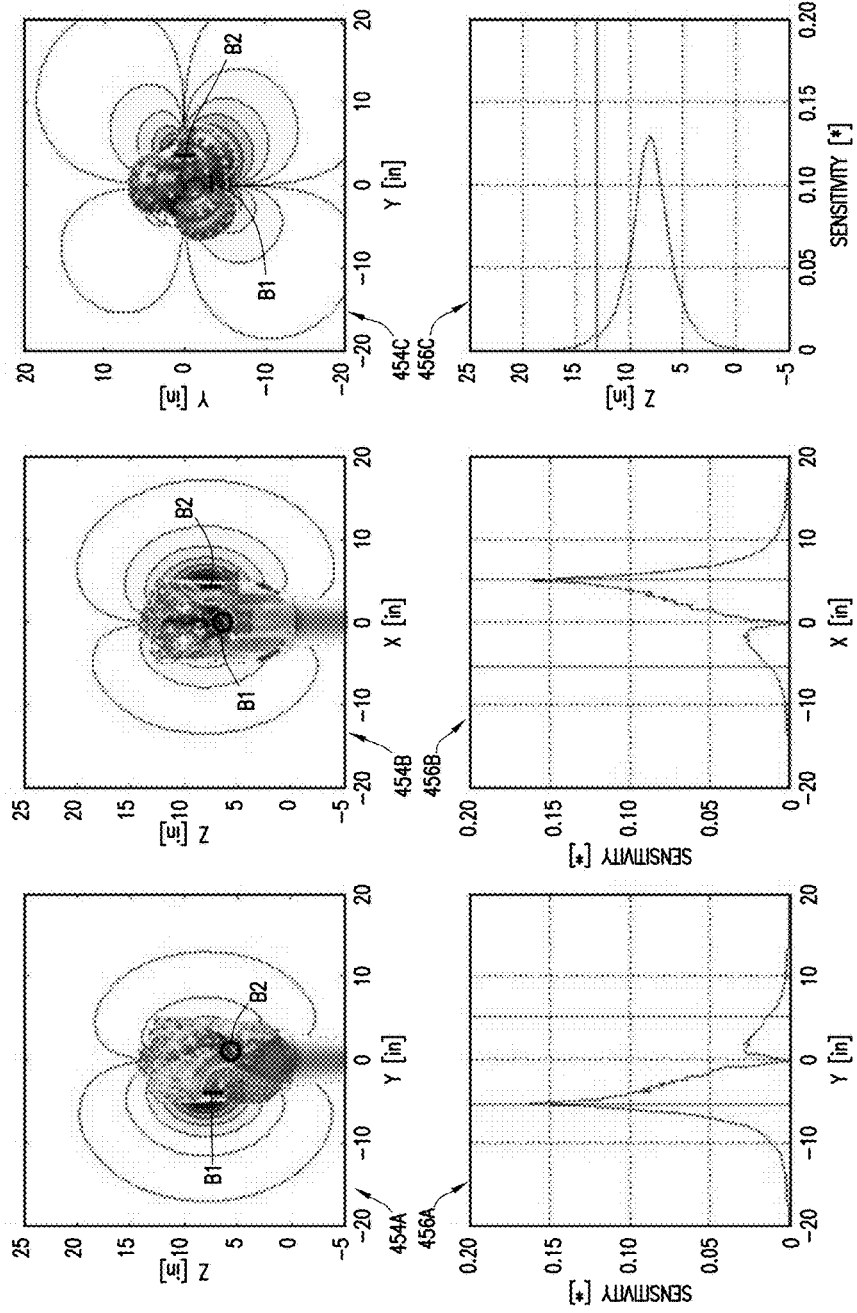

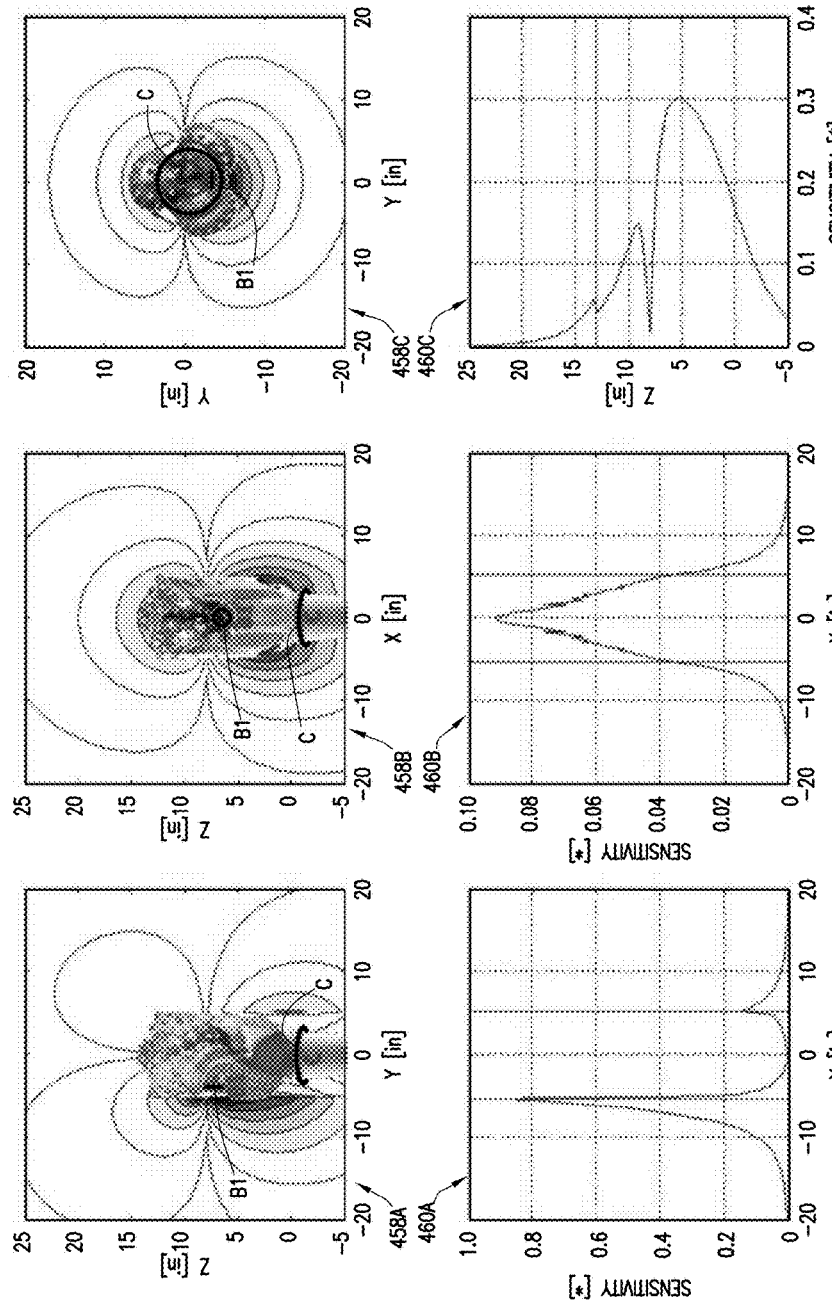

ROLLER CONE RESISTIVITY SENSOR

CROSS-REFERENCE TO RELATED APPLICATION

The present application is a U.S. National Stage Application of International Application No. PCT/US2014/073039 filed Dec. 31, 2014, which is incorporated herein by reference in its entirety for all purposes.

TECHNICAL FIELD

The present disclosure relates generally to well drilling operations and, more particularly, to systems and methods for taking resistivity measurements of a formation using a roller cone drill bit.

BACKGROUND

Hydrocarbons, such as oil and gas, are commonly obtained from subterranean formations that may be located onshore or offshore. The development of subterranean operations and the processes involved in removing hydrocarbons from a subterranean formation typically involve a number of different steps such as, for example, drilling a wellbore at a desired well site, treating the wellbore to optimize production of hydrocarbons, and performing the necessary steps to produce and process the hydrocarbons from the subterranean formation.

Modern well drilling operations require precise steering controls and operations to land boreholes in thin bed hydrocarbon reservoirs, while avoiding undesirable formation strata. Such steering operations may require that a borehole start on a generally vertical trajectory and transition to a horizontal trajectory as it nears a particular formation strata boundary, so as to land in the desired formation strata. Tools that generate electromagnetic waves can be used to investigate the surrounding formation for strata boundaries, but at long distances, due to the presence of multiple layers in typical formations and low tool sensitivity far from the borehole, the tools have limited effectiveness at identifying formation boundaries. Although resistivity sensors can be disposed in a bottom hole assembly (BHA) of the drilling string, precise placement of the wellbore into thin bed reservoirs is still generally difficult with sensors in the BHA due to depth lag. The lack of accurate deep formation measurements makes it difficult to identify the formation boundary early enough for the borehole to land effectively in the desired formation strata.

BRIEF DESCRIPTION OF THE DRAWINGS

For a more complete understanding of the present disclosure and its features and advantages, reference is now made to the following description, taken in conjunction with the accompanying drawings, in which:

FIGS. 12A-12C are a series of plots illustrating sensitivity measurements of a roller cone drill bit having one receiver antenna, in accordance with an embodiment of the present disclosure;

FIGS. 13A-13C are a series of plots illustrating sensitivity measurements of a roller cone drill bit having one transmitter antenna and one receiver antenna, in accordance with an embodiment of the present disclosure;

FIGS. 15A-15C are a series of plots illustrating sensitivity measurements of a roller cone drill bit having one transmitter antenna and one receiver antenna, in accordance with an embodiment of the present disclosure;

FIGS. 16A-16C are a series of plots illustrating sensitivity measurements of a roller cone drill bit having one transmitter antenna and one receiver antenna, in accordance with an embodiment of the present disclosure;

FIGS. 17A-17C are a series of plots illustrating sensitivity measurements of a roller cone drill bit having one transmitter antenna and one receiver antenna, in accordance with an embodiment of the present disclosure;

DETAILED DESCRIPTION

Figure 1:
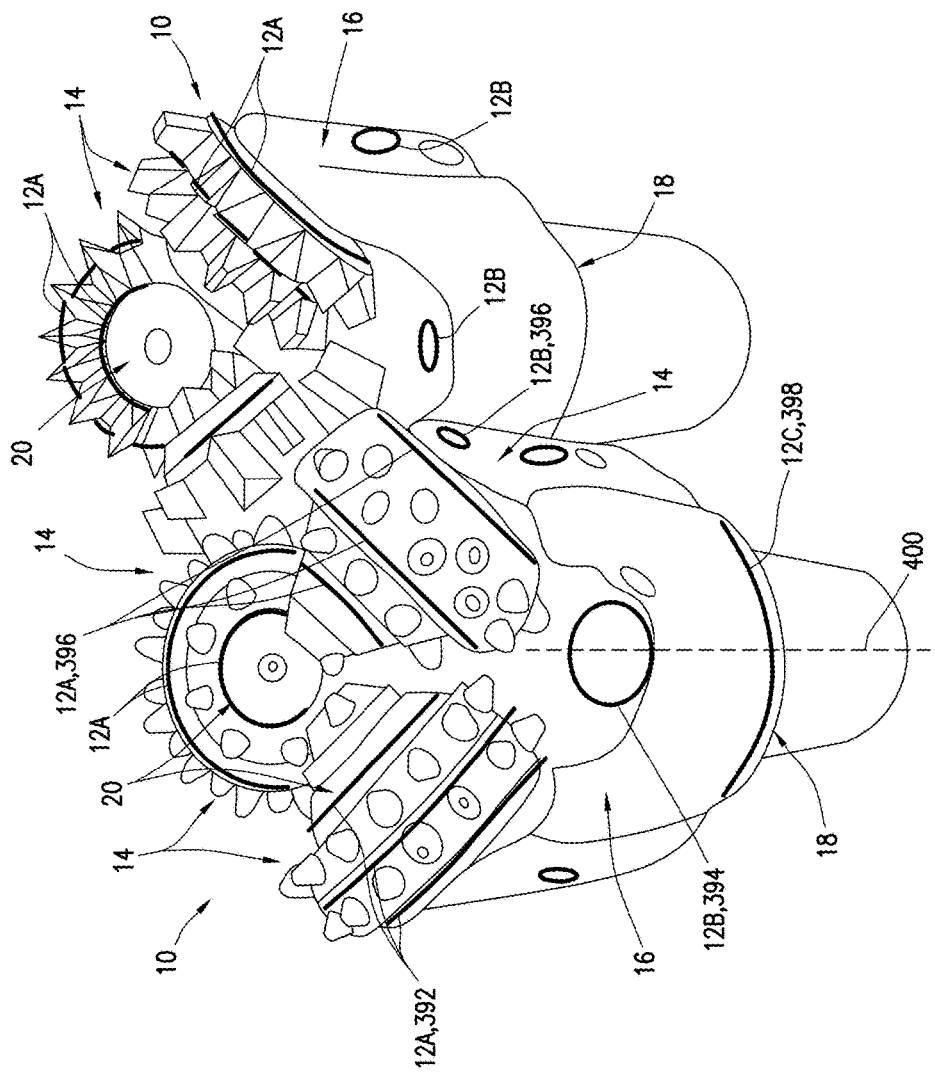
FIG. 1 is a perspective view of two roller cone drill bits showing various locations for antenna loops to be disposed on the drill bits, in accordance with an embodiment of the present disclosure.

Illustrative embodiments of the present disclosure are described in detail herein. In the interest of clarity, not all features of an actual implementation are described in this specification. It will of course be appreciated that in the development of any such actual embodiment, numerous implementation specific decisions must be made to achieve developers' specific goals, such as compliance with system related and business related constraints, which will vary from one implementation to another. Moreover, it will be appreciated that such a development effort might be complex and time consuming, but would nevertheless be a routine undertaking for those of ordinary skill in the art having the benefit of the present disclosure. Furthermore, in no way should the following examples be read to limit, or define, the scope of the disclosure.

Certain embodiments according to the present disclosure may be directed to a drilling system that uses a roller cone drill bit with an antenna loop disposed therein to enable certain measurements to be taken from the bit. For example, the drilling system may utilize one or more antennas disposed in the roller cone drill bit to enable resistivity measurements of a subterranean formation. Two antennas are generally used to take such resistivity measurements. One or more antennas act as a transmitter that transmits electromagnetic energy into the formation based on a current that is supplied to the transmitter antenna. One or more antennas act as receivers that receives or intercepts a portion of the electromagnetic energy reflected off the formation and outputs a voltage and phase difference from the transmitter phase for measurement.

Taking resistivity measurements from the drill bit may be important for enabling proper "look-ahead" and "look-around" resistivity sensing. Look-ahead sensing refers to the ability of the drilling system to detect certain properties of the formation at a location ahead of the drill bit while the drilling system is being lowered to drill the wellbore. Look-around sensing refers to the ability of the drilling system to detect formation properties at a location surrounding the portion of the wellbore being drilled.

Existing systems typically utilize a resistivity sensing system that is built into a logging while drilling (LWD) or measuring while drilling (MWD) module disposed within the bottom hole assembly (BHA) of the drill string. Such modules are located above the drill bit in the drilling string and, thus, do not reach the depth of the wellbore that the bit is drilling into until after the drill bit has moved beyond that point. In some instances, for example, the sensing equipment in the LWD or MWD modules may not reach the depth that a drill bit is drilling into until about 5 to 6 hours after the drill bit has drilled there. This time difference can be even worse while drilling deviated wells. The existing resistivity sensors in the MWD/LWD modules typically do not have the depth of field in the antennas used to perform the resistivity measurements to provide the desired look-ahead and look-around measurements needed to make real-time changes in drilling course based on the measurements. However, in present embodiments, the antennas used to perform these measurements may be located directly at the bit. From this position, the antenna does not need as much depth of field, and thus can provide more accurate look-ahead and look-around resistivity measurements with which to adjust drilling parameters in real-time.

Again, the one or more antennas disposed in the roller cone drill bit may be used to detect a resistivity of the formation through which the drill string is being lowered. The resistivity measurement may inform certain decisions to change a course of drilling or to adjust various other drilling parameters to more drill more effectively. The resistivity measurement may provide drilling operators information regarding the material of the formation, since each material in the formation has a particular resistivity.

The resistivity measurement may also provide information regarding the amount of anisotropy in the formation. That is, the formation may include layers of different types of rock, sand, shale, and other materials. The layers may vary in thickness and in the direction in which they extend. It may be desirable in some drilling operations to determine the anisotropic direction of the formation. The anisotropic direction refers to the direction in which the drill string can travel through the formation so that it passes quickly through several different layers of the formation. In some formations this may be a substantially vertical direction, while in others it may be a more deviated direction. Drilling in the anisotropic direction may enable the drilling system to more efficiently pass through formation layers to find a desired formation section for production. Once the desired formation layer is found, it may be desirable to then steer the drill bit in a direction that aligns a larger portion of the drill string with the formation (e.g., isotropic direction).

The geometry of the roller cone drill bit may be particularly suitable for collecting resistivity measurements that are used to determine anisotropy in a subterranean formation. Specifically, the roller cones on this type of drill bit tend to be mounted in a slanted orientation with respect to the axis of the drill bit itself as it extends into the wellbore. By providing the antenna loop in the slanted roller cone portion of the drill bit, the antenna loop may provide resistivity measurements of different depths of the formation as well as different radial positions of the formation surrounding the drill bit. These measurements may be interpreted to determine variations in resistivity of the formation that may indicate anisotropy. In addition, such measurements may be performed with as few as just the one antenna loop disposed in the roller cone drill bit.

Other applications of the antenna in a roller cone drill bit may include using a resistivity sensor in the drill bit as a magnetic or electromagnetic ranging system. Such ranging sensing refers to detection of how close or far the drilling system is from a boundary of the formation or a nearby target. For example, electromagnetic or magnetic ranging can be utilized at the drill bit to follow an existing borehole or to intersect an existing borehole to drill a relief well in the case of a blowout. In other operations, electromagnetic or magnetic ranging may enable relativistic steering of the drill string to a bed boundary or formation resistivity value, in order to maintain the drill string traveling in an oil bearing zone rather than in an aquifer. Taking these measurements via an antenna disposed in the roller cone drill bit may give an operator more room to make adjustments when trying to intersect a well or follow an oil bed boundary.

As mentioned above, one or more antenna loops may be disposed in a roller cone drill bit. The roller cone drill bit may include one or more roller cones disposed therein that are rotatably coupled to a stationary part of the drill bit (e.g., journal arm) in order to cut away rock from the formation more effectively. That is, the roller cones may be attached to the journal arm in such a way that enables the roller cones to rotate relative to the journal arm of the drill bit. Roller cone drill bits, both insert and mill tooth varieties, typically are considered a cheap alternative to fixed cutter bits such as polycrystalline diamond compact (PDC) drill bits. In addition, in some rock types it is more economical to run a roller cone drill bit than a PDC drill bit. Thus, PDC drill bits with sensors and other instrumentation are a relatively costly way to provide any desired look-ahead look-around resistivity measurements. The disclosed roller cone drill bit is generally cheaper to manufacture and operate within certain wellbores than the fixed cutter bits. Presently disclosed embodiments provide a roller cone drill bit having an antenna loop disposed in the roller cone portion of the bit, in order to perform specific types of resistivity or magnetic ranging measurements from the bit.

In some embodiments of the disclosed system, the roller cone drill bit may include just a receiver antenna loop. For example, a transmitter antenna disposed in an upper portion of the drilling system (e.g., BHA) may transmit electromagnetic waves into the formation, and the antenna loop disposed in the roller cone drill bit may intercept the waves from the formation to provide the measurement. This may enable the system to provide resistivity detection at a point close to the bottom of the drill string without requiring additional electronic components to be disposed in the replaceable bit portion.

In other embodiments the roller cone drill bit includes both transmitter and receiver antenna loops. It may be desirable to position these transmitter and receiver antenna loops in certain positions relative to one another within the drill bit. For example, the transmitter and the receiver antennas may be disposed in an orthogonal orientation relative to one another. That is, the plane in which one of the antenna loops is oriented may be substantially perpendicular to the plane in which the other antenna loop is oriented. This orthogonal sensor placement may increase the dynamic range of the resistivity measurement, since the electromagnetic waves are able to propagate from the transmitter into the formation instead of traveling straight through the receiver from the transmitter antenna.

Different arrangements of transmitter and/or receiver antennas in the roller cone drill bit may facilitate resistivity measurements that are suitable for drilling different types of formations. As described in detail below, some sensor arrangements may enable resistivity measurements of very high sensitivity within a small spatial range surrounding the drill bit, while others may enable measurements that have a larger range but lower resolution. In addition, some sensor arrangements may provide more detailed measurements of the resistivity on one side of the drill bit (e.g., azimuthal measurement). Such arrangements may be particularly suitable for drilling formations where it is desirable to focus on one area of rock in the formation.

FIG. 1 illustrates a pair of roller cone drill bits 10 that are equipped with sensing components at different points along the roller cone drill bits 10. Specifically, these sensing components may include loop antennas disposed about the roller cone drill bits 10 at certain positions 12 to provide desired resistivity measurements or magnetic ranging measurements. These positions 12 may include, but are not limited to, the roller cones 14 of the drill bits 10, on side surfaces 16 of the drill bits 10, or about a circumference 18 of a base of the drill bit 10.

Although three cones 14 are illustrated in each roller cone drill bit 10, other embodiments of such drill bits 10 may include from one to six or more cones 14. Certain positions 12 on such roller cones drill bits 10 may offer geometries suitable for placement of a loop antenna. The illustrated embodiment shows several possible, but not limited, positions 12 for loop dipole electromagnetic wave antennas. In particular, an antenna may be disposed along a ring 12A about one of the cones 14 of the drill bits 10. This position 12A may be particularly desirable location to place a tilted or off-axis loop antenna, since an incident force from the bottom of the hole on the drill bit 10 does may not directly impinge on this part of the drill bit 10 when weight is applied on the bit 10. In addition, as mentioned above, the tilted orientation of the antenna in this position 12A may enable the drilling system to make anisotropic measurements of the formation using a single antenna loop disposed on the roller cone 14. In some embodiments, the outermost ring position 12A of a roller cone 14 may represent a location that provides enhanced durability and survivability of the antenna loop placed thereon.

It should be noted that other locations 12 on the drill bit may be utilized besides the rings 12A on the cones 14. For example, in other embodiments the loop antenna may be disposed on the bit shank (12B), around the body of the bit (12C), and/or around the flow nozzle of the drill bit 10.

In some embodiments, multiple antenna loops may be disposed on the same outer face 20 of the roller cone 14, this face 20 being designed to contact the bottom of the wellbore hole during drilling operations to advance the wellbore. In such embodiments of the drill bit 10, each of the multiple antenna loops may feature different diameters, due to the grooves that may be formed in the cones 14 for insertion of the antennas as the desired positions 12A or to accommodate the milled teeth on the cone 14 that are designed to mesh with other cones 14. Accordingly, some antennas on the bit face 20 may be different sizes because of the positioning of the insert teeth and the grooves to accommodate neighboring cones 14. However, as long as the diameter of each of the antennas disposed in their specific positions 12 is known, these positions 12 may function as antenna sites for resistivity sensors to providing ranging or proximity sensing.

Figure 2A:
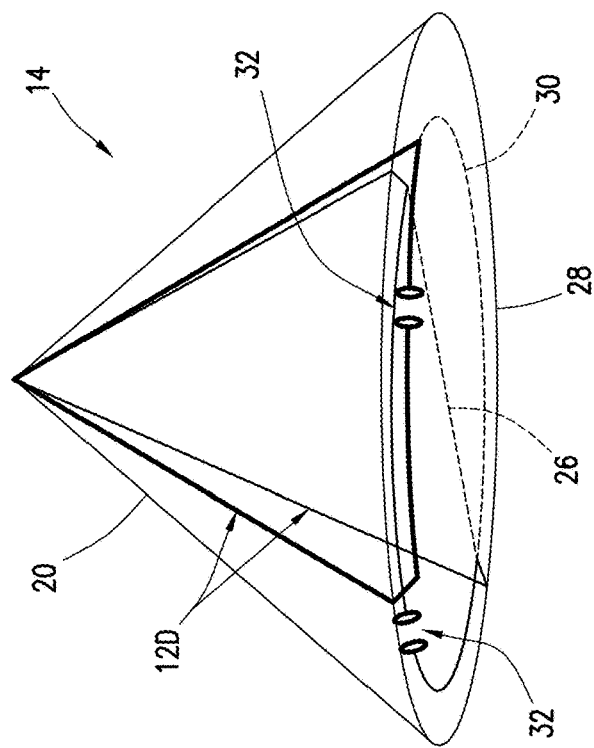
FIGS. 2A and 2B are schematic perspective views of two roller cones having antenna loops disposed thereon, in accordance with an embodiment of the present disclosure.
Figure 2B:
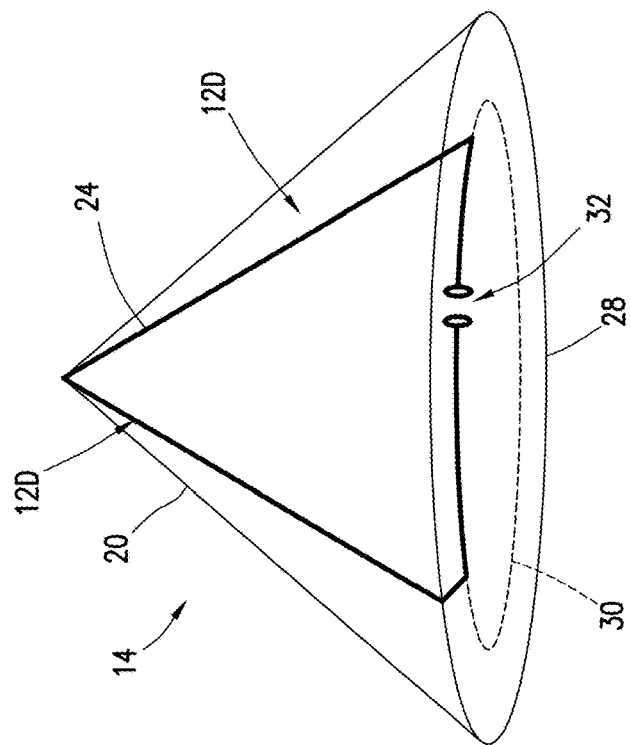

FIG. 2 illustrates another embodiment showing other positions 12D that may be used for the placement of antennas 24 on a roller cone drill bit 10. In the schematic illustration, two representative roller cones 14 of a roller cone drill bit 10 are shown having antennas 24 placed in certain loop paths 12D. No roller cone teeth are illustrated, in order to provide a simplified figure. As illustrated, each loop path 12D may primarily cut across a diameter 26 of the roller cone 14 following a shape that generally tracks the outer face 20 of the cone 14. When the path 12D arrives at a circular face 28 of the cone 14, it may then loop along a circumferential path 30 around the face 28 to complete the loop. At some point along this circumferential path 30, there may be a break 32 in the antenna 24 along the loop to connect antenna wires to the antenna 24. However, it should be noted that the break 32 in the antenna 24 may occur at any desired point along the antenna path 12D in other embodiments.

Figure 3:
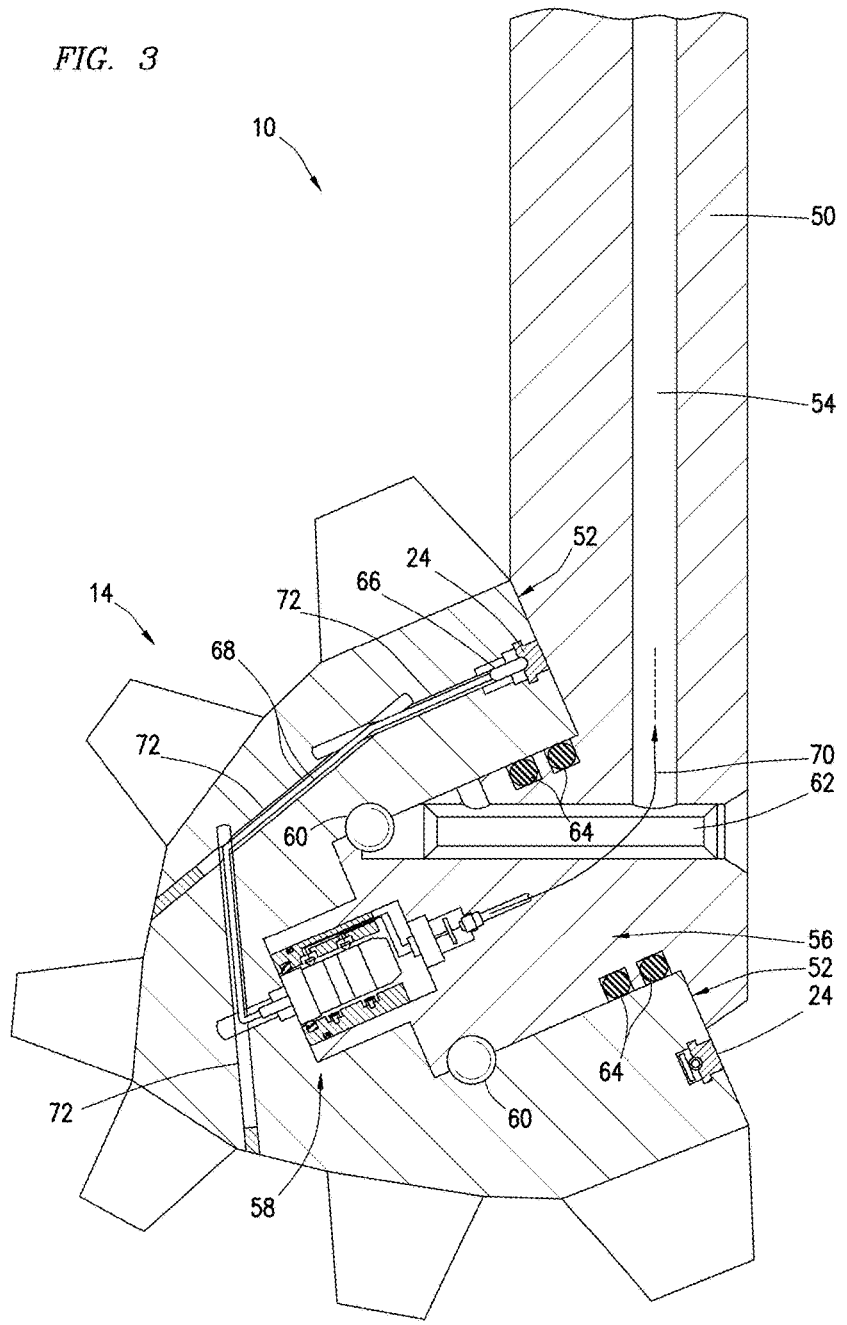
FIG. 3 is a schematic cross-sectional view of a roller cone drill bit having an antenna loop disposed in a roller cone, in accordance with an embodiment of the present disclosure.

Having now described general placements of the antenna loop 24 on roller cones 14 for use in the disclosed drill bit system, a more detailed description of the drill bit system components will be provided. FIG. 3 schematically illustrates a cross section of a roller cone 14 and a shank 50 that may be present in the roller cone drill bit 10. As illustrated, the roller cone 14 may feature the above described antenna loop 24 for carrying out the desired resistivity measurements. Specifically, the antenna loop 24 is disposed circumferentially around a back portion 52 of the roller cone 14 (opposite the portion of the roller cone 14 that impacts the wellbore). However, it should be noted that in other embodiments the antenna 14 may be disposed along other diameters of the roller cone 14 and may not necessarily follow a circular path depending on the geometry of the desired general path direction for the roller cone antenna or antenna on the bit body. Non-circular paths may be a result of routing the antenna around teeth inserts, for example, which may form a more erratic loop path or around the shank, which may be more oval due to the shape of the shank. In general, though, all antennas may have a loop path, meaning that the beginning and end point of the antenna will at least partially loop around some path and generally return back to a position proximate the starting point of the other end of the antenna.

In some embodiments, the drill bit 10 may include the shank 50, the cone 14, a hydrostatic pressure balance channel 54 that connects to a balance piston or diaphragm (not shown), a journal arm 56, a cone slip ring and electronics assembly 58, a ball bearing retention ring 60, a ball bearing retainer (not shown), and a retention pin 62. The shank 50 may provide structural support for the roller cone 14 and may couple the illustrated roller cone 14 to other similar roller cones 14 of the drill bit 10. The ball bearing retention ring 60 and ball bearing retainer may be used to hold bearings in place between the journal arm 56 and the roller cone 14, thereby allowing the roller cone 14 to rotate with respect to the journal arm 56 during drilling. The hydrostatic pressure balance channel 54 passing through the shank 50 may provide a pathway for routing oil from a diaphragm pump to the ball bearings in the retention ring 60. The retention pin 62 may seal the pressure balance channel 54 from the pressure outside the drill bit 10 so as to maintain the channel 54 at hydrostatic pressure after assembling the bearings into the drill bit 10. Additional O-ring seals 64 may be disposed between the journal arm 56 and the roller cone 14.

The antenna loop 24 disposed in the roller cone 14 may include two ends 66 (only one is visible) for connecting opposite ends of the antenna wire to other electronic components used to perform resistivity or magnetic ranging calculations. Each of the ends 66 may be coupled to a respective wire 68 through the roller cone 14 that transmits electronic signals between the antenna loop 24 and other electronic components. As illustrated, these wires 68 may be routed through the cone slip ring and electronics assembly 58 of the roller cone 14. For example, the roller cone 14 may include channels 72 that are machined into and sealed within the cone 14 to facilitate a path for the wires 68 leading from the antenna loop 24 to the cone slip ring and electronics assembly 58. The channels 72 may include plugs 74 formed in the ends of the channels 72 that would otherwise extend outside the roller cone 14. It should be noted that the illustrated embodiment is one example of a roller cone 14 having a built-in antenna loop 24 for taking resistivity and other measurements, and other types, shapes, and arrangements of the roller cone 14 may exist in other embodiments.

The cone slip ring and electronics assembly 58, as described in detail below, may enable the signals to be routed from the rotating roller cone 14 to the relatively stationary journal arm 56. In some embodiments, the cone slip ring and electronics assembly 58 may include electronics designed to filter and/or amplify or otherwise alter signals sent to or from the antenna loop 24. Additional wires 70 may be coupled to an end of the cone slip ring and electronics assembly 58 opposite the roller cone 14 and used to route signals to or from another electronics assembly further up the bottom hole assembly (BHA) to which the drill bit 10 is attached. To that end, these wires 70 may pass through the already present pressure balance channel 54. This may simplify assembly of the roller cone drill bit 10, since an additional channel does not have to be machined to carry the wires 70 through the shank 50.

Figure 4:
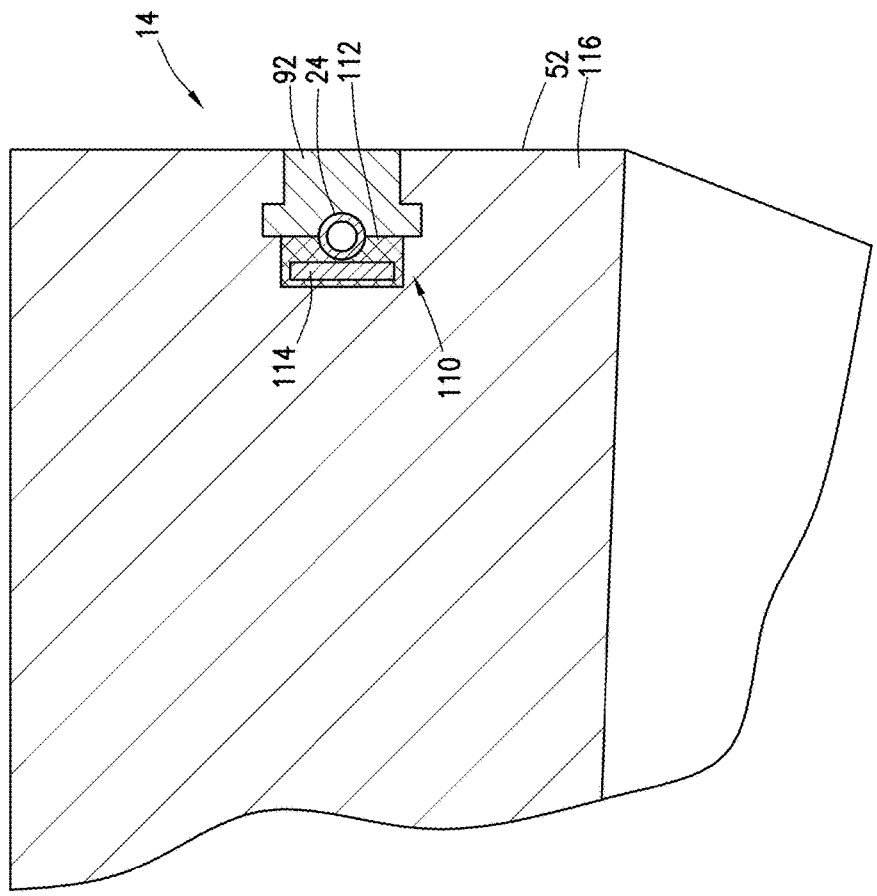
FIG. 4 is a schematic cross-sectional view of the antenna loop disposed in the roller cone of FIG. 3, in accordance with an embodiment of the present disclosure.

FIG. 4 illustrates a cross section of an antenna assembly 110 having the antenna loop 24 placed within an edge of the roller cone 14. It should be noted that other arrangements of antenna assemblies 110 may be used to accommodate the disclosed antenna loop 24 within other embodiments of the roller cone 14. In the illustrated embodiment, the antenna assembly 110 includes the antenna loop 24, a focusing element 92, a molding component 112 (e.g., potting material), and a ferrite rod 114.

The focusing element 92 may be a radial focusing element 92 of the antenna loop 24 disposed in a groove formed in the body 116. The radial focusing element 92 may aid in focusing the electromagnetic field and offer erosion protection of the antenna loop 24. The radial focusing element 92 may also provide some structural support of the antenna loop 24. The focusing element 92 may be made from metal and, in some embodiments, may be coated with a dielectric to prevent it from allowing eddy currents to flow across the back face 52 of the roller cone 14. In other embodiments, the focusing element 92 may be made integral to a body 116 of the roller cone 14 by using a 3D metal printer to print the focusing element 92 within the body 116. In other embodiments, the focusing element 92 may be uninsulated and in electrical contact with the cone body 116.

In the illustrated embodiment, the antenna loop 24 is a hollow tube. However, in other embodiments, the antenna loop 24 may include a solid tube. The antenna loop 24 may be made from a metal such as titanium, copper, silver, a metal alloy, or some other electrically conducting material. In some embodiments, the antenna loop 24 may be made from a lamination of materials, such as a core of stainless steel with an overlay layer of another material with a higher conductivity. For example, the overlay layer may be constructed from copper, silver, graphene, carbon nanotubes, or any other suitable conductor. The overlay may be layered with a desired thickness based on the intended operating minimum frequency of the antenna loop 24. In addition to the core and the overlay layer, some antenna loops 24 may also be coated with a dielectric layer to keep the current on the antenna and to reduce any chance of the current shorting to the roller cone 14, particularly if the cone 14 becomes damaged. Thus, the dielectric coating may provide a redundant layer of protection for the antenna loop 24. The dielectric coating may include a layer of polyether ether ketone (PEED) such Arlon 1000, polytetrafluoroethylene (PTFE), nylon, teflon, or some other suitable insulator.

Most often the materials used in traditional roller cone drill bits are made of a high strength metal that is relatively cheap to manufacture, such as a ferrous alloy steel. However, in some embodiments the cone body 116 and/or the bit body may be made from a non-magnetic material such as P550, Monel® or inconel, titanium, aermet, or some other non-magnetic metal or metal alloy. By making the cone and/or bit body out of a non-magnetic material, it may be possible to reduce the inductance the antenna 24 will see when it drives an electromagnetic wave into its surroundings through AC current excitation injected into the loop antenna 24. Some embodiments of the roller cone 14 may also feature inserts 118 extending from the body 116 to cut into the formation. Such inserts 118 may be formed from any desirable hard material, such as polycrystalline diamond compact (PDC) or tungsten carbide inserts with a non-magnetic binder material (other than pure cobalt). If the cone body 116 is non-magnetic, as described above, the antenna assembly 110 may benefit from a ferrite (e.g., ferrite rod 114) or other highly magnetically permeable material disposed around at least a portion of the antenna loop 24. This ferrite rod 114 may enhance an H-field magnitude (magnetic field strength) generated from current flowing through the antenna loop 24. This in effect may increase the inductance back to a more desired level for the magnetic path of the signal. Hence, depending on the desired frequency, it may be desirable to use some ferrous parts for the bit if it is beneficial for tuning the resonance of the antenna 24 at a desired frequency and/or adding ferrite or other ferrous materials in the antenna loop 24 such as by making the cone out of a ferrous material.

The illustrated molding material 112 may be used to fill up the space between the components of the antenna assembly 110, in order to keep cuttings and fluid from entering the antenna area. In some embodiments, the molding material 112 may include a plastic material (e.g., epoxy, ceramic, rubber, nylon, Teflon, or PEEK) injection molded into the spaces around the antenna loop 24, the ferrite rod 114, and against the focus element 92. In other embodiments, the molding material 112 may be constructed as solid parts that are later inserted to fill in the extra area within the roller cone 14. Other materials that may be used from the molding material 112 include rubber or any other non-conducting material.

Figure 5:
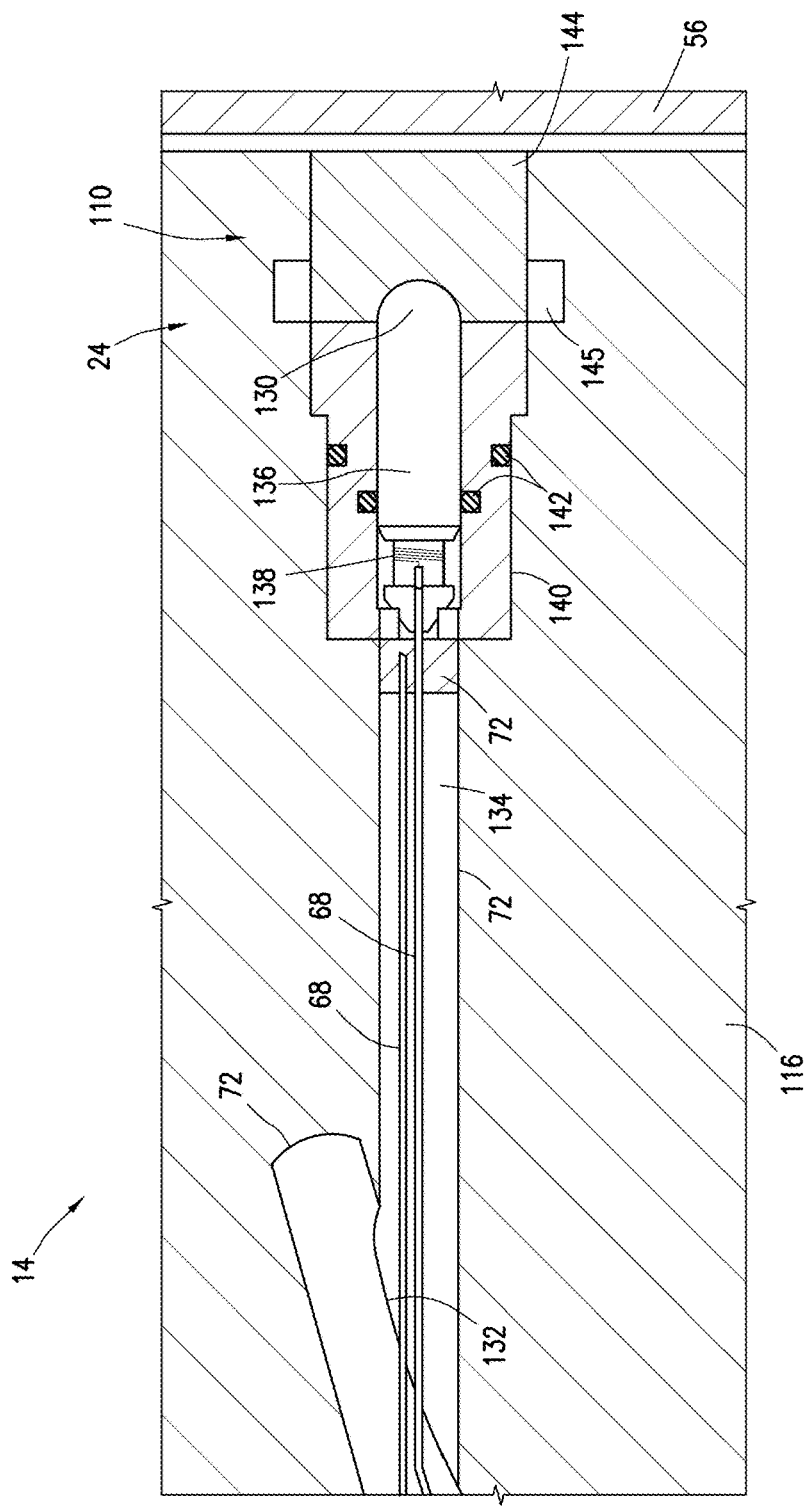
FIG. 5 is a schematic cross-sectional view of an antenna stub disposed in the roller cone of FIG. 3, in accordance with an embodiment of the present disclosure.
Figure 6:
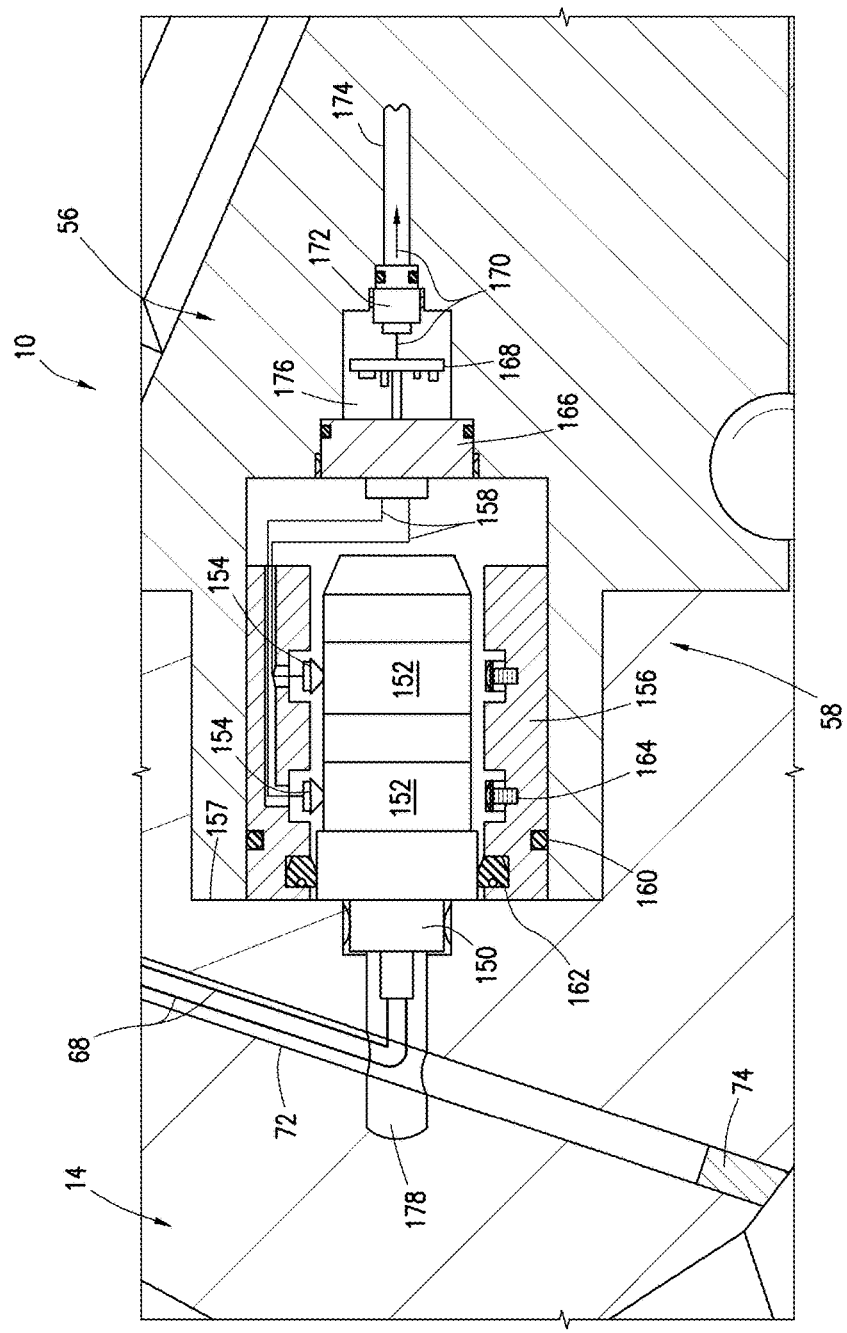
FIG. 6 is a schematic cross-sectional view of a slip ring assembly disposed in the roller cone of FIG. 3, in accordance with an embodiment of the present disclosure.

FIGS. 5 and 6 illustrate more detailed views of the components that may be present in the roller cone 14. For example, FIG. 5 focuses on the antenna post insertion point of one end 130 of the antenna loop 24. The illustrated embodiment includes two wires 68 as described above. As shown in the cross-sectional view, one of the wires 68 is connected to the antenna end 130 while the other extends into the page toward the other antenna loop end (not shown). It should be noted that, although only one insertion point is shown at one end 130 of the antenna loop 24, a similar arrangement may exist for the opposite end of the antenna loop 24. The wires 68 may be any desired type of conductor. These wires 68 may be routed to the slip ring in the thrust bearing area of the roller cone 14, as described in detail below. In some embodiments, one end of the antenna loop 24 may be grounded to the roller cone body 116 so that only one insulated wire 68 is connected to the other end of the antenna loop 24 to convey the current through the antenna. However, this technique may limit the ability to control a flow path of the current and thus the direction of electromagnetic radiation within the antenna loop 24. Although illustrated as parallel wires 68, the two wires 68 coupled to the ends of the antenna loop 24 may be disposed within a two conductor cable, such as a twisted pair of cables or a coaxial cable.

As mentioned above, the wires 68 may follow a path pre-machined or formed channels 72 through the body 116 of the roller cone 14. The channels 72 may be formed during a casting, 3D printing, or electrical discharge machining (EDM) construction of the base metal forming the body 116. In other embodiments, the channels 72 may be drilled as holes into the body 116. In such instances, it may be desired to overshoot the channels 72 relative to each other to ensure a full intersection 132 of the channels 72 with each other. The channels 72 may create a path for the wires 68 to traverse from the slip ring portion of the roller cone 14 to the antenna loop ends 130.

During construction of the roller cone 14, it may be desirable to displace all air from the channels 72 with a fluid such a lubrication fluid, so that pressure compensation piston or diaphragm can be used to pressure balance the fluid inside the roller cone fluid lubrication area with the outside wellbore pressure as the bit is lowered into the wellbore. This may allow the rotary seals to operate in a balanced pressure situation, thereby increasing the life of the rotary seals. This displacement of air through the channels 72 may also be accomplished by potting the path with a fill material 134, such as a solidifying plastic or ceramic epoxy, rubber, or a plastic injection. In this case, a fluid communication path may be formed between the channels 72 and the cone bearing area, which is already in fluid communication with the pressure balance system of the roller cone 14 as described above.

As illustrated, the wire 68 may follow a path defined by the channels 72 to connect to the antenna end 130. The antenna end 130 may include an antenna stub 136 that protrudes approximately perpendicular to the antenna loop 24 itself. In some embodiments, the wire 68 could be coupled to the antenna stub 136 via a connector. However, in the illustrated embodiment, the bare conductor portion of the wire 68 may be soldered directly to the antenna stub 136 via a soldering groove 138 formed within the antenna end 130.

In some embodiments, the antenna stub 136 may be seated into an electrically insulated post carrier 140. This carrier 140 may be made from a PEEK material, for example, or some other type of machinable plastic. The carrier 140 may include seals 142 on it to prevent drilling fluid from entering the back side of the antenna assembly 110 or the channels 72. A retainer cap 144 having a dielectric insulative coating, such as the above described focus elements 92, may be used to hold the antenna loop 24 in place. The retainer cap 144 may be mounted in the roller cone 14 via mounting grooves 145 formed therein. The retainer cap 144 may then be secured with a small bolt or other fastener (not shown). In other embodiments, the retainer cap 144 may be secured to the roller cone 14 via any other desirable fastening method including, but not limited to, brazing, welding, or gluing. Further potting material 134 may be disposed in the space between the retainer cap 144 and the antenna loop 24 to fill up the assembly and also to aid in binding the retainer cap 144 to the roller cone 14.

FIG. 6 illustrates in detail the interface between the journal arm 56 and the roller cone 14, focusing on the cone slip ring and electronics assembly 58 among other components. The wires 68 routed from the antenna loop 24 via the channels 72 may feed into a connector 150 that is secured (e.g., threaded) to the roller cone body 116. The wires 68 may then feed to individual conductor rings 152, one for each wire 68. Spring contacts 154 may be disposed around each of the respective conductor rings 152 to permit electrical contact between the spring contacts 154 and the conductor rings 152. Thus, as the roller cone 14 rotates relative to the journal arm 56 during drilling, electrical contact can be maintained between the wires 68 to the antenna loop 24 and electrical components on the journal-arm side of the drill bit 10.

The spring contacts 154 may be coupled to a non-conducting spring carrier 156. The spring carrier 156 may be constructed from PEEK (such as Arlon 1000) since it is a machinable plastic that is non-conductive, although other materials may be used in other embodiments. The spring carrier 156 may be disposed along a thrust bearing face 157 of the journal arm 56 and secured to the journal arm 56 via a fastener, threads, or chemical bonding process to ensure that the spring carrier 156 does not rotate relative to the journal arm 56. Such undesirable rotation of the spring carrier 156 would lead to breakage of insulated wires 158 leading away from the spring carrier 156. The spring carrier 156 may also include seals 160 disposed thereon to maintain a desired pressure in the space between the journal arm 56 and the spring carrier 156. In some embodiments, the spring carrier 156 may also be equipped with a wiper barrier 162 disposed between the rotatable slip ring components and the stationary spring carrier 156. The spring contacts 154 may be fastened to the spring carrier 156 at slip ring spring fastener points 164 along the spring carrier 156.

It should be noted that several other techniques may be utilized to enable electrical transmission across two bodies that are rotating at different speeds or, in this case, where one is stationary while the other is rotating. For example, in some embodiments, the system may utilize an inductive coupling of two electric coils to mutually induce electrical energy like a transformer from one coil to the other. Other forms of slip rings may be used in other embodiments. In addition, a toroid coupling could be used wherein inner electrical contact is made to facilitate local loop currents that impart the energy coupling between two toroids. However, the illustrated slip ring embodiment may be particularly appropriate for use in the roller cone drill bit 10 to provide a relatively clear connection within the desired size constraints.

The insulated wires 158 leading away from the spring carrier 156 may correspond to a receiver antenna or a transmitter antenna, depending on a downhole or pre-run selectable antenna configuration. In embodiments where the antenna loop 24 is configured to operate as a receiver antenna, additional electronic components may be disposed in the journal arm 56 to provide processing of electrical signals at the drill bit 10. As illustrated, the wires 158 may run through a feed through connector (or pressure bulkhead) 166 to a circuit board 168 in the journal arm 56. The circuit board 168 may include a band pass filter, pre-amp or amplifier circuit to boost the sensed signal strength, and an impedance matching circuit that can improve the response of the receiving antenna selectively tuned or fixed to a transmit frequency of the sensor system transmitter. In some embodiments, the circuit board 168 may also include a digitizing circuit that can be utilized to convert the sensed analog signal transmitted from the wires 158 into a digital return signal to be delivered to a sensor controller.

In some embodiments, the assembly may include a shielded sensor cable 170 carrying all the conductor leads away from the circuit board 168. The leads in the sensor cable 170 may carry power, ground, and the sensor signal to and from the circuit board 168. The sensor cable 170, once through an additional pressure bulkhead 172, may travel along a path or channel 174 through the drill bit 10 (e.g., through the pressure balance channel 54 of FIG. 3) to a separate sensor controller system for further processing. The sensor controller will be described in detail below.

In the illustrated embodiment, the circuit board 168 is generally disposed in a pressure vessel 176 formed between pressure bulkheads 166 and 172. The bulkheads 166 and 172 may include seals that maintain a desired pressure within the vessel 176 to support proper functioning of the electronics on the circuit board 168.

It should be noted that the use of electronics, specifically the circuit board 168) at this position of the journal arm 56 is optional. In other embodiments, it may be desirable to route the signals from the antenna loop 24 all the way from the antenna loop 24 to the sensor controller via the wires 68 and 158 disposed in the drill bit 10, without any intervening electronic processing. However, by including these minimal support electronics (e.g., circuit board 168) in the drill bit 10, it may be possible to improve the signal to noise ratio of the sensor signal from the antenna that would otherwise worsen over the distance from the drill bit 10 to the sensor controller. Thus, it may be desirable to use an AC/DC converter in the circuit board 168 to digitize the received sensor signal at this portion of the drill bit 10 (if space permits), as this digitization may increase the accuracy of the sensor. Digital filters may also be included in the circuit board 168 if desired, in order to further refine the received signal. However, it should be noted that such digital filters may be applied later at any point along the bit stream from the drill bit 10 to the sensor controller without loss of signal fidelity due to distance.

Although the circuit board 168 with the above described electronics is illustrated in the journal arm portion of the drill bit 10, in other embodiments the circuit board 168 may be disposed at a position 178 within the roller cone 14, before the sensor signal passes through the slip ring. In still further embodiments, the circuit board 168 and corresponding electronics may be disposed in the roller cone 14 along with a toroid that is able to communicate via local loop currents with another toroid disposed further up the drill bit 10 or on another portion of the BHA. In such embodiments, the illustrated slip ring assembly may not be necessary, since the processed sensor signal is able to be communicated directly from the roller cone 14 to the sensor controller.

Having now generally described the components used to communicate sensor signals from the antenna loop 24 through the roller cone drill bit 10, a detailed description of the components used to communicate these signals between the roller cone 14 and a sensor controller will be provided. The sensor controller may be either in the drill bit 10 or in a near-bit sub.

Figure 7:
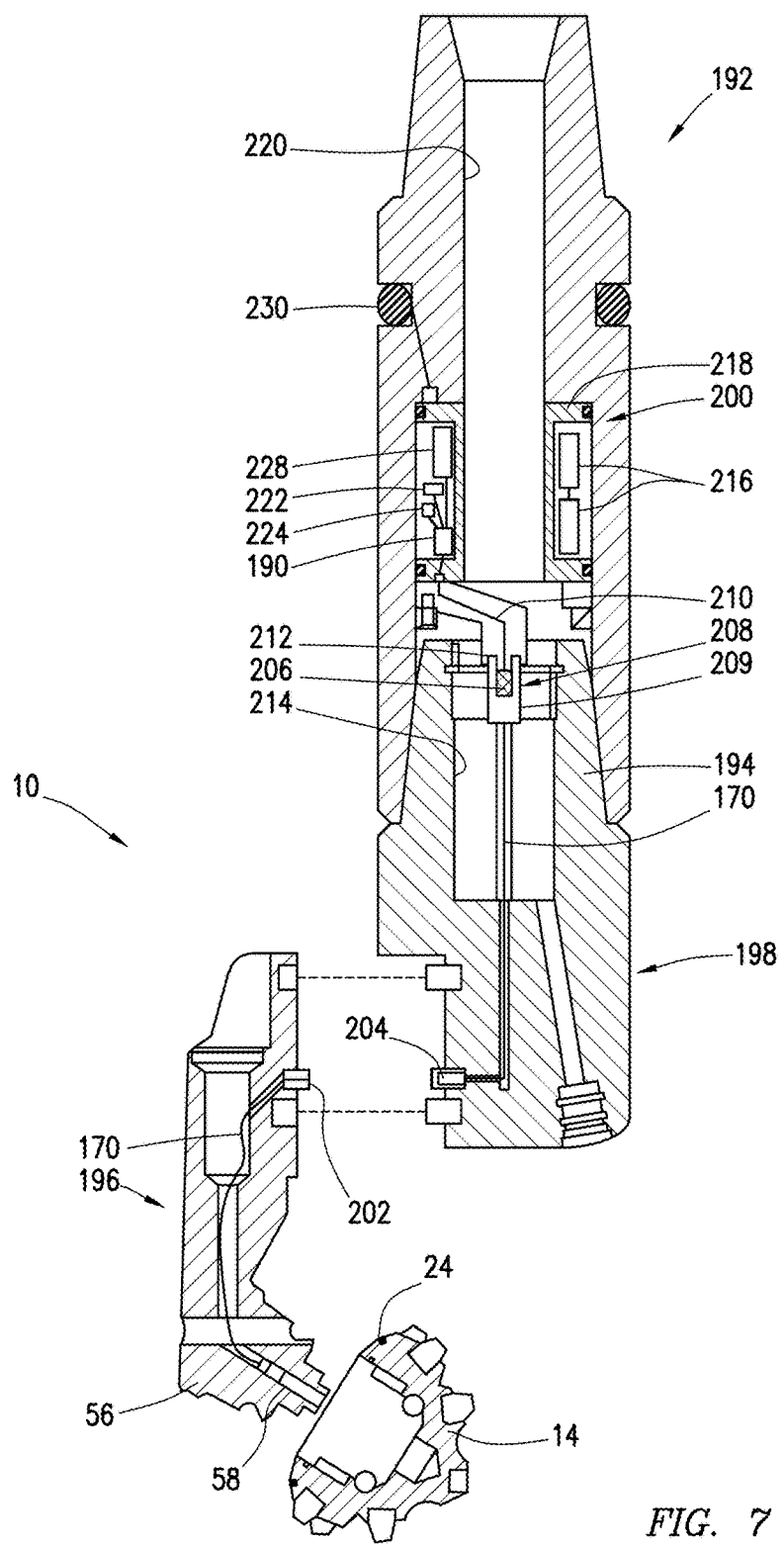
FIG. 7 is a schematic cross-sectional view of the drill bit of FIG. 3 coupled to an instrument sub, in accordance with an embodiment of the present disclosure.

FIG. 7 is a diagram of the roller cone drill bit 10 with the antenna loop 24 in which an associated sensor controller 190 for the antenna loop 24 is located in an instrument sub 192 coupled to a threaded end 194 of the bit 10, according to aspects of the present disclosure. Like the bit 10 described above, the antenna loop 24 is located in the roller cone 14 rotationally coupled to the journal arm 56. Again, the drill bit 10 may include a slip ring and electronics assembly 58 for routing a sensor signal from the antenna loop 24 within the roller cone 14 into the journal arm 56 and filtering and/or digitizing the signal. The journal arm 56 may be extending from a leg 196 coupled to a bit body 198 of the drill bit 10, and may be communicably coupled to the sensor controller 190 and associated electronics 200 through the wire or cable 170. In other embodiments, the roller cone drill bit 10 containing the antenna loop 24 may also include some or all of the associated electronics 200 therein, instead of containing them in an outside location such as the sub 192.

In the embodiment shown, a first portion of the cable 170 couples the slip ring and electronics assembly 58 to a connector 202 on the leg 196, and a second portion of the cable 170 couples a connector 204 on the bit body 198 to another connector 206. The connector 202 may be positioned to align with the connector 204 when the leg 196 is coupled to the bit body 198, and may facilitate removal of the leg 196 from the bit body 198, although the leg 196 does not have to be removable. When the leg 196 is integral with the bit body 198, the connectors 202 and 204 may be omitted, and a single, uninterrupted cable 170 may be run from the slip ring and electronics assembly 58 through the leg 196 and the bit body 198 to the connector 206.

The connector 206 may provide an interface to removably couple the antenna loop 24 via the cable 170 to the sensor controller 190 in the instrument sub 192. In the embodiment shown, the connector 206 may include a plunger-type connector 206 in which the female portion of the connector 206 is coupled to the cable 170, and also coupled to the drill bit 10 through a lock-ring/groove engagement 208 in an inner chamber 209 of the bit body 198. Conversely, the male portion of the connector 206 is coupled to the sensor controller 190 and other associated electronics 200 through a cable 210, coupled to the sub 192 through a retainer ring and fastener 212, and aligned to engage with the female portion when the instrument sub 192 is coupled to the drill bit 10. The relative positions of the male and female portions with respect to the bit 10 and sub 192 may be switched, as can the manner in which the male and female portions are respectively coupled to the bit 10 and instrument sub 192. Likewise, other connector types and configurations are possible, including inductive couplings that are located outside of an internal chamber 214 of the bit body 198.

In the embodiment shown, the associated electronics 200 may include the sensor controller 190 and a power source 216 located within a sealed housing 218. The sealed housing 218 may protect the associated electronics 200 from a flow of drilling fluid through an internal bore 220 of the sub 192, as will be described in detail below. Both the sensor controller 190 and power source 216 may be coupled to the connector 206 through the cable 210. The power source 216 may include power storage elements, such as batteries, or power generation elements, such as turbines, etc.

In some embodiments, for example, the power source 216 may include a power generator including a turbine with permanent magnets of alternating polarity affixed to its outer surface and positioned within corresponding coils. A flow of drilling fluid through the internal bore 220 may cause the turbine to rotate and current to be generated within the coils due to the alternating polarity of the permanent magnets. In certain instances, the power source 216 may include power storage elements, such as rechargeable batteries or super capacitors, coupled to the coils in order to store energy generated by the coils and provide the stored energy to the gamma ray detector when the turbine is not rotating. In certain embodiments, the associated electronics 200 may further include a high voltage power supply coupled to the power source 216, through which power from the power source 216, either directly from the coils or indirectly from the coils through the power storage elements, is supplied to the antenna loop 24 or other electric components in the drill bit 10. Other types, combinations, and configurations of power generators and storage elements may be used within the scope of this disclosure, including vane turbines coupled to a center shaft generator. Additionally, the power generator described herein may be adapted for use in the drill bit 10 described above.

Power from the power source 216 may be provided to the antenna loop 24 and/or slip ring and electronics assembly 58 through the cables 210 and 170. In certain embodiments, the power source 216 may be coupled to the cables 210 and 170 and therefore the antenna and associated bit electronics though a high voltage power supply 222. The sensor controller 190 may perform some or all of receiving sensor signals from the antenna 24 through the cables 170 and 210; storing, processing, and/or transmitting to another control unit the received sensor measurements; and transmitting control signals to the antenna loop 24 and/or bit electronics through the cables 170 and 210. As used herein, a control unit may include a device that contains at least one processor communicably coupled to a non-transitory computer readable memory device containing a set of instructions that when executed by the processor, cause it to perform certain actions. Example processor include microprocessors, microcontrollers, digital signal processors (DSP), application specific integrated circuits (ASIC), or any other digital or analog circuitry configured to interpret and/or execute program instructions and/or process data.

In certain embodiments, the associated electronics 200 may include other electrical elements, such at least one additional sensor. In the embodiment shown, the at least one additional sensor includes a gyroscope 224 and a magnetometer 226, both of which are coupled to the sensor controller 190. The sensor controller 190 may receive measurements from all of the antenna loop 24, gyroscope 224, and magnetometer 226. The measurements from the gyroscope 224 and magnetometer 226 may identify the rotational orientation of the sub 192 and drill bit 10 when the measurements were taken at the antenna loop 24. In certain embodiments, the sensor controller 190 may process the measurements received from the antenna loop 24 by correlating those measurements with the corresponding rotational orientation of the drill bit 10.

In certain embodiments, the associated electronics 200 may further include a communications system to allow sensor controller 190 to transmit the received and/or processed measurements of the antenna loop 24 to another control unit for storage or processing. In the embodiment shown, the communication system may include a communications interface 228 coupled to the sensor controller 190 and a toroid 230 coupled to the interface 228 and positioned on an outer surface of the sub 192. The toroid 230 may be one of a pair of toroid that can be used to establish a short-hop telemetry system using modulated electromagnetic (EM) signals for bi-directional data transmission, with the other toroid being located away from the toroid 230 by a short distance, such as 30 feet, or at another point in the drill string. This other point in the drill string may include a surface location around the well head, in the fashion of the EM telemetry used for long haul telemetry systems. Other methods can also be employed on surface for bidirectional communication using an electrode in the ground near the wellhead and a wire running from the well head and the electrode to a surface EM transceiver. Although a short-hop EM telemetry system is shown, other types of communications systems may be used in other embodiments, including wired communications systems in which a connector is integrated into the sub 192, other long-haul or short hop telemetry systems, using acoustic, torsional, or mud pulse communication mechanisms, or a combination of two or more telemetry systems. A combination of telemetry systems may be implemented either simultaneously in parallel or in a conversion method from one telemetry format to another, such as converting EM or acoustic short hop telemetry to mud pulse long haul telemetry to and/or from the surface.

Figure 8:
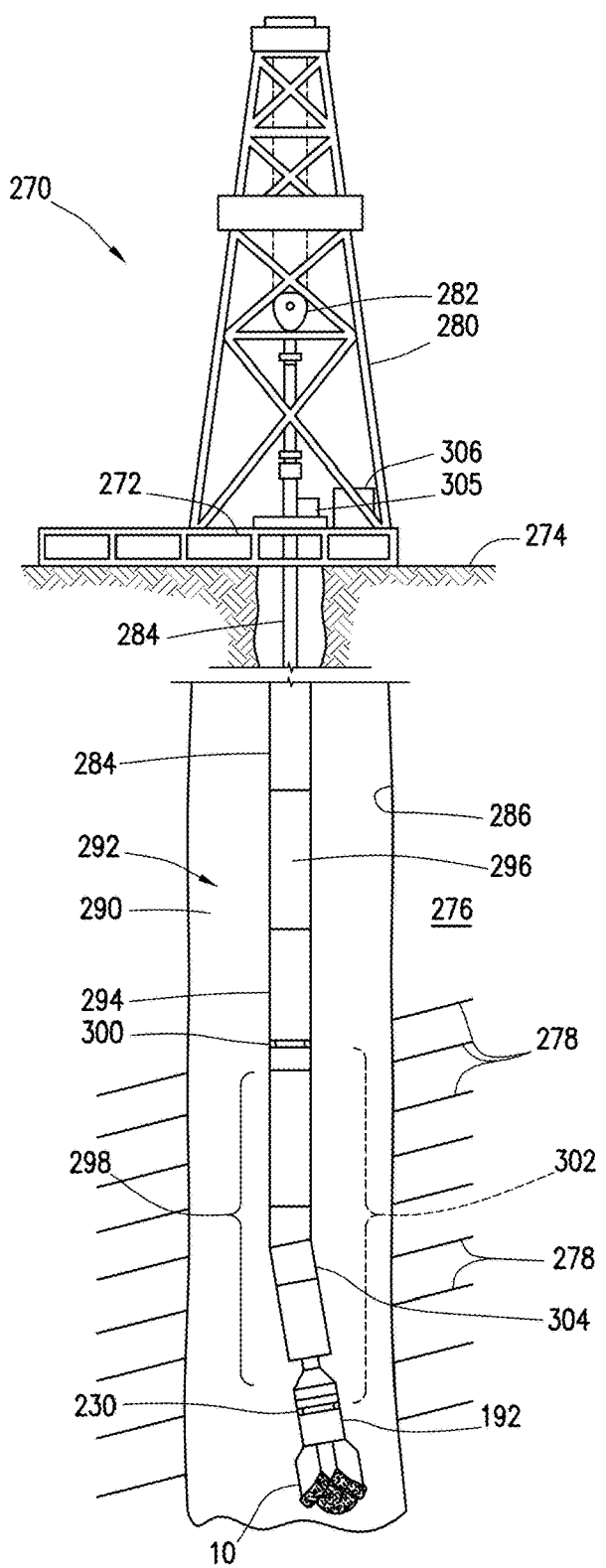
FIG. 8 is a schematic illustration of a drilling system utilizing a roller cone drill bit with an antenna loop disposed therein, in accordance with an embodiment of the present disclosure.

FIG. 8 is a diagram of an example drilling system 270 incorporating a roller cone drill bit 10 an antenna loop 24 for resistivity or magnetic ranging detection (not shown), according to aspects of the present disclosure. The drilling system 270 may include a drilling platform 272 positioned at a surface 274. In the embodiment shown, the surface 274 includes the top of a formation 276 containing one or more rock strata or layers 278, and the drilling platform 272 may be in contact with the surface 274. In other embodiments, such as in an off-shore drilling operation, the surface 274 may be separated from the drilling platform 272 by a volume of water. A derrick 280 may be supported by the drilling platform 272 and have a traveling block 282 for raising and lowering a drill string 284 through a wellbore 286 created by the drill bit 10.

The drill bit 10 may be coupled to the drill string 284 and driven by a downhole motor and/or rotation of the drill string 284 by a rotary table and kelly, or by a top drive. In the embodiment shown, the drill bit 10 is coupled to the drill string 284 through the instrument sub 192 containing associated electronics for the antenna loop 24 in the drill bit 10. This includes the toroid 230 of a short-hop EM telemetry system similar to those described above. In other embodiments, a drill bit 10 in which the associated electronics are located in the bit 10 may be used. A pump may circulate drilling fluid through a feed pipe to a kelly, downhole through the interior of drill string 284, through orifices in the drill bit 10, back to the surface via an annulus 290 around the drill string 284, and into a retention pit. The drilling fluid transports cuttings from the wellbore 286 into the pit and aids in maintaining integrity or the wellbore 286.

The drilling system 270 may further include a bottom hole assembly (BHA) 292 coupled to the drill string 284 near the drill bit 10. The BHA 292 may include various downhole measurement tools and sensors, such as LWD/MWD tools 294, as well as a telemetry system 296, and downhole motor 298. A corresponding toroid 300 to the toroid 230 in the instrument sub 192 may be located within and coupled to a control unit of the BHA 292, and may establish an EM telemetry channel 302 between the BHA 292 and the instrument sub 192. In the embodiment shown, the toroid 300 is coupled to the LWD/MWD tool 294, although such a configuration is not required.

The LWD/MWD tool 294 may include different types of sensors that may collect measurements of the formation 276 surrounding the tool 294 and the BHA 292 generally. In certain embodiments, the LWD/MWD tool 294 may include a control unit (not shown) coupled to the sensors that receives and stores measurements from the sensors, processes the measurements, and/or transmits those measurements to a different control unit in the drilling system. In the embodiment shown, the toroid 300 may be coupled to the control unit within the LWD/MWD tool 294, and the control unit may treat toroid 300 as another sensor in the LWD/MWD tool 294 and the signal received through the toroid 300 as a corresponding measurement of the toroid 300. Because the signal received through the toroid 300 corresponds to the electrical signal generated by the antenna loop 24, the control unit of the LWD/MWD tool 294 may effectively treat the antenna loop 24 as a resistivity sensor of the LWD/MWD tool 294, even though the detector is located in the drill bit 10.

The downhole motor 298 may include a downhole mud motor that generates torque in response to the flow of drilling fluid through the drill string 284 and applies that torque to the drill bit 10. In the embodiment shown, the downhole motor 298 further includes a bent housing 304 that causes the drill bit 10 to drill at an angle with respect to the drill string 284. In certain embodiments, the bent housing 304 may be adjustable such that the drilling angle may be altered downhole, allowing the drill bit 10 to be "steered" during the drilling process. In other embodiments, separate steering tools or devices may be used in addition to or instead of the motor 298 and bent housing 304 to steer the drill bit 10. For example, when torque at the drill bit 10 is generated by the rotary table or top drive through the drill string 284, rather than through the motor 298, one or more of a point-the-bit and push-the-bit type rotary steerable systems may be used to alter the angle of the drill bit 10. The drill bit 10 may be steered to intersect one of the formation strata 278 that contains hydrocarbons, avoid certain undesired strata or formation bodies, follow an existing borehole, or intersect an existing borehole to drill relief wells in the case of a blowout.

The tools and sensors of the BHA 292 may be communicably coupled to the telemetry system 296. The telemetry system 296 may itself include a control unit (not shown) and may transfer measurements and signals from the BHA 292 to a surface receiver 305 and/or to receive commands from the surface receiver 305. The telemetry system 296 may include a mud pulse telemetry system, an acoustic telemetry system, a wired communications system, a wireless communications system, or any other type of communications system that would be appreciated by one of ordinary skill in the art in view of this disclosure. In certain embodiments, some or all of the measurements taken at the BHA 292 may also be stored for later retrieval at the surface.

In certain embodiments, the drilling system 270 may include a surface control unit 306 positioned at the surface. In certain embodiments, the surface control unit 306 may provide additional functionality not available at the control units within the wellbore 286, such as a keyboard and monitor that allow a user at the surface to interact with the surface control unit 306. The surface control unit 306 may be communicably coupled to the surface receiver 305 and may receive measurements and signals from the BHA 292 and/or transmit commands to the BHA 292 though the surface receiver 305. Due to the lack of size constraints at the surface, the surface control unit 306 typically has greater processing capability that the control units located downhole.

When the drilling system 270 is in use, the drill bit 10 may rotate and extend the wellbore 286 through a portion of the formation 276 in front of the drill bit 10. The resistivity detector (e.g., antenna loops 24) within the drill bit 10 may detect a resistivity of the portion of the formation 276 in front or to the sides of the drill bit 10, and generate a corresponding electrical signal, as described above. This corresponding electrical signal may include look ahead and look around measurements, which may be processed by one or more control units within the drilling system to determine at least one characteristic of the portion of the formation 276. Example characteristics include the geometry of the portion, the composition of the portion, and the location and orientation of a boundary between two rock strata within the portion. In certain embodiments, once determined, the characteristic may be used to make a decision with respect to the operation of the drilling system 270. For example, if the characteristic of the portion includes the location of the boundary between strata, the decision may include altering a drilling angle of the drill bit 10 at the motor 298, or stopping the drilling process before the boundary is crossed.

Figure 9:
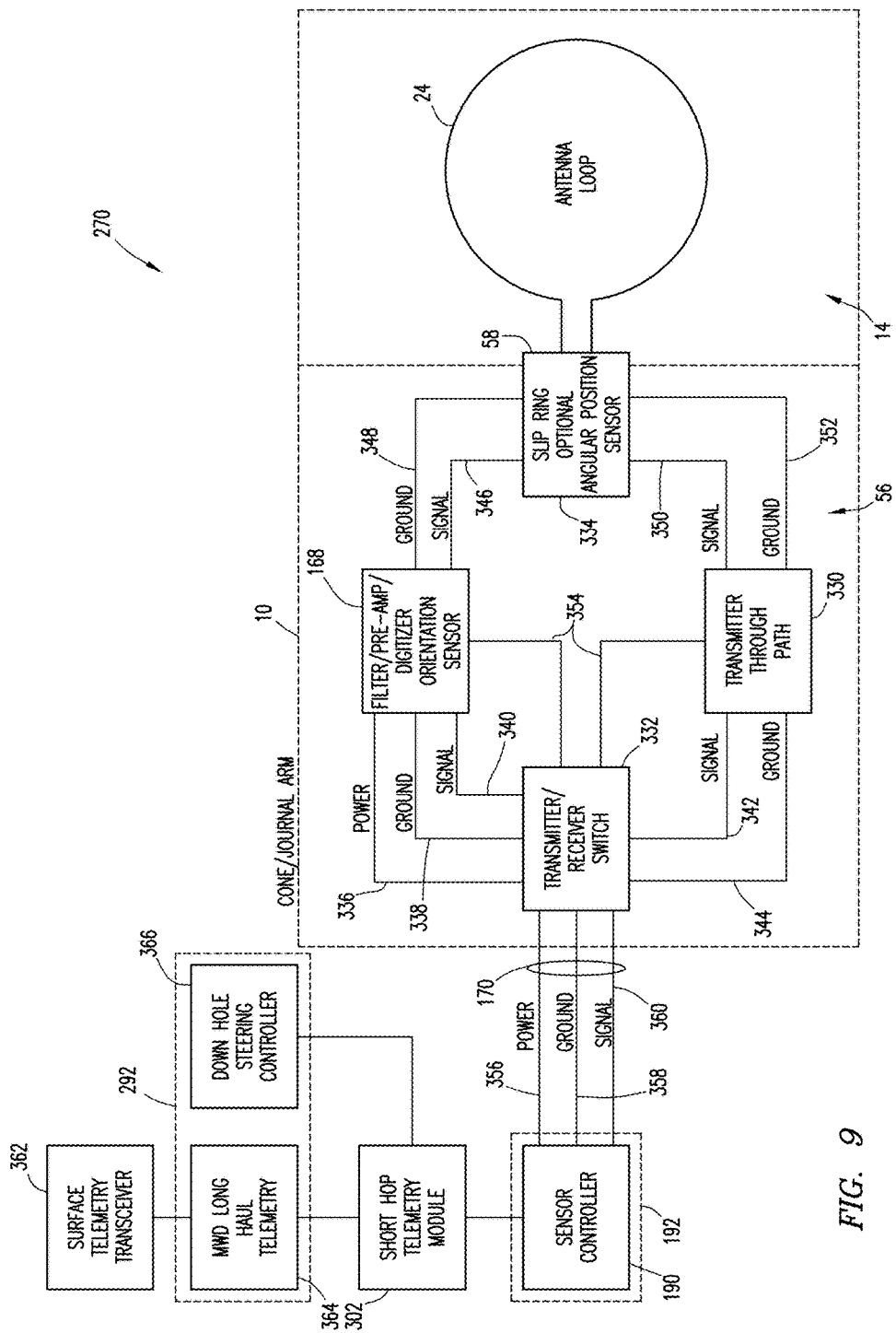
FIG. 9 is a block diagram of a drilling system utilizing a roller cone drill bit with an antenna loop disposed therein, in accordance with an embodiment of the present disclosure.

FIG. 9 is a block diagram of the drilling system 270, according to aspects of the present disclosure, and illustrates the control units and electrical elements of the drilling system 270. As mentioned above, these control units and electrical elements may be used to generate, transmit, store, and/or process the look ahead and look around measurements from the drill bit 10. The illustrated diagram of the drilling system 270 also includes communications channels and signals that may be present between the electrical elements to facilitate the generation, transmission, storage, and/or processing of the look ahead or look around measurements. As can be seen, the drill bit 10 includes the antenna loop 24 and optional associated electronics, which may be coupled to the sensor controller 190 and other electronics within the instrument sub 192.

In some embodiments, it may be desirable to minimize the amount of electronics present within the roller cone 14 of the roller cone drill bit 10. This may reduce the cost of the roller cone 14 in the bit, which is likely to become damaged or need to be replaced, while maintaining relatively expensive electronic items away from the roller cone 14 so that they do not become consumed during erosion of the drill bit 10 as a result of drilling. This may be particularly useful if the antenna loop 24 disposed in the roller cone 14 is elected to be used as a transmitter antenna. In this case, it may be desirable to position all support electronics for the transmitter antenna loop 24 in the sensor controller 190 instead of in the drill bit 10. Indeed, in such embodiments the roller cone 14 (or the entire drill bit 10) with the inlaid antenna loop 24 may be designed as an item that can be thrown away after a certain amount of use of the drill bit 10 and then replaced. In embodiments where the antenna loop 24 is going to be used as a receiver, the roller cone 14 with the antenna loop 24 may be a throw-away part that can be replaced, while at least portions of the cone slip ring and electronics assembly 58 within the journal arm 56 may be recovered for use in a new drill bit 10.

Accordingly, the layout illustrated in FIG. 9 represents one embodiment of the drilling system 270, while other arrangements of the illustrated components may be utilized in other embodiments. In the illustrated arrangement, the drilling system 270 includes an optional configuration for allowing the loop antenna 24 to be selectively switched between a transmitter or a receiver. Specifically, this configuration may include a circuit component (e.g., circuit board 168), a transmitter through path 330, a transmitter/receiver switching mechanism 332, and a slip ring 334. In some embodiments, the circuit board 168 may include a filter, a pre-amp or other amplifier, a digitizer, an orientation sensor, or some combination thereof. In addition, the slip ring 334 may be equipped with an optional angular position sensor that detects the angular position of the roller cone 14 based on the measurement taken at the slip ring 334. Other arrangements of these position and orientation sensors may be utilized within the drill bit 10 to determine individual and respective distances and orientations of the roller cone 14 compared to the formation or to other roller cones of the drill bit 10.

As illustrated, the cone slip ring and electronics assembly 58 of the drill bit 10 may be coupled together via multiple control lines, which may include conductors routed between the components. For example, the transmitter/receiver switch 332 may be coupled to the circuit board 168 via three lines, which may include a power line 336, a ground line 338, and a signal line 340. Similarly, the transmitter/receiver switch 332 may be coupled to the transmitter through path 330 via two lines, a signal line 342 and a ground line 344 to carry a signal to or from the antenna loop 24. Further, the circuit board 168 may be coupled to the slip ring 334 via two lines, a signal line 346 and a ground line 348 to carry the electrical signal to or from the antenna loop 24. Still further, the transmitter through path 330 may be coupled to the slip ring 334 via two lines, a signal line 350 and a ground line 352 to carry the electrical signal to or from the antenna loop 24. The circuit board 168 and the transmitter through path 330 may also be coupled to the transmitter/receiver switch 332 via control lines 354 used to communicate a state of the transmitter/receiver switch 332 to these components.

As illustrated, the transmitter/receiver switch 332 may also be coupled to the sensor controller 190 via three lines, which may include a power line 356, a ground line 358, and a signal line 360. These three lines may be present within the above described sensor cable 170 running from the drill bit 10 to the instrument sub 192. The power lines 336 and 356 may transmit a flow of power from a power supply (e.g., in the sensor controller 190) to the circuit board 168 and to the transmitter/receiver switch 332, respectively. The signal lines 360, 340, 342, 346, and 350 and ground lines 358, 338, 344, 348, and 352 may facilitate a flow of electrical current from the sensor controller 190 through the antenna loop 24, or from the antenna loop 24 to the sensor controller 190, depending on a state of operation of the antenna loop 24.

The transmitter/receiver switch 332 may be used to switch the operating mode of the antenna loop 24 based on a signal from the sensor controller 190. Specifically, the transmitter/receiver switch may provide control signals via the control lines 354 to the circuit board 168 and to the transmitter through path 330 based on a desired operating mode for the antenna loop 24. In some embodiments, another wire could be run from the sensor controller 190 to the transmitter/receiver switch 332 to signal this switching function. In other embodiments, a DC voltage bias may be applied (e.g., across the power line 356) to enact the transmitter/receiver switch 332. In some embodiments, the switch 332 may include a solid state relay, a field effect transistor (FET), a mechanical relay, or some other switching device to enable a configuration of the electronics so that the antenna loop 24 acts as either a transmitter or a receiver. The signal for enacting the switch 332 may be generally managed by the sensor controller 190, which contains a processor, memory, a power source either hard wired from the drill string or locally generated or supplied by batteries/capacitors.

It should be noted that there may be a plurality of transmitters and receivers used at any given time with a plurality of different transmit frequencies to selectively control the kind of measurement desired. For example, if there is a bed boundary below the sensor in a horizontal wellbore, it may be desirable to use a combination of transmitters and receivers that are selectively turned on as the loop antenna's focus sweeps across the low side of the wellbore to better concentrate the measurement in a desired direction of concern. The antennas 24 may be synchronously activated as the drill bit 10 rotates and the desired antenna loops 24 come within range. This may conserve power so as not to expend energy sweeping other portions of the hole where the resistivity measurement is no concern. In other embodiments, selective phasing of the signals using both antenna loop positions and frequencies between the various antennas may be employed to create a focused synthetic aperture in a desired direction to detect a higher response in a particular direction.

In another embodiment, the sensor may be used to detect highly conductive man-made structures or man-made objects embedded in the formation nearby, such as the casing or liner of another wellbore or a lost in-hole drill string in an adjacent well. The resistivity sensor can be selectively tuned by changing frequencies or selecting certain antennas 24 on the drill bit 10 for improved detection of such man-made structures or objects, instead of formation properties. For example, an appropriate responsive frequency for measuring formation resistivity may not necessarily be the best frequency for detecting casing structures in the formation.

In other embodiments, the antenna loop 24 may include a plurality loops in the form of an antenna winding, which would enable the antenna 24 to operate more efficiently at lower frequencies for a deeper depth of penetration. Winding layers may reach up to approximately 60,000 loops for very low frequency transmissions. In this case, the antenna wire would likely have to be a very fine magnetic wire typically wound onto the drill bit roller cone 14 or the bit body.

In operation, when the antenna loop 24 is to be operated as a transmitter, the sensor controller 190 may signal the transmitter/receiver switch 332 to configure the circuit board 168 and the transmitter through path 330 as desired. For example, the circuit board 168 may not need to filter and digitize any sensor signal since the antenna loop 24 is transmitting and not receiving. From here, the sensor controller 190 may output an electrical signal through the transmitter through path 330 and to the antenna loop 24 so that the antenna loop 24 may transmit the desired signal into the formation being drilled.

When the antenna loop 24 is to be operated as a receiver, the sensor controller 190 may signal the transmitter/receiver switch 332 to configure the circuit board 168 and the transmitter through path 330 as desired. For example, the switch 332 may signal the circuit board 168 to provide the desired sensor filtering, amplification, and/or digitization for the incoming sensor signal. From here, a signal (e.g., a portion of a transmitted signal that is reflected off the formation) may be received via the antenna loop 24, processed via the electronics on the circuit board 168, and directed to the sensor controller 190 for further processing. During transmission or receiving signals via the antenna loop 24, the other sensors (e.g., orientation sensor or angular position sensor) disposed on the drill bit 10 may be used to measure other factors relating to drill bit operation while the antenna loop 24 is gathering or emitting signals.

In instances where the antenna loop 24 is acting as a receiver, it may be desirable to provide the collected resistivity measurement data to a surface mounted control unit, as described above. To that end, the illustrated drilling system 270 may include additional components coupled to the sensor controller 190. As described above, the sensor controller 190 may be coupled to a toroid of the instrument sub 192, and the sensor controller 190 may transmit either the processed or raw measurements from the antenna loop 24 over the bi-directional short-hop EM telemetry channel 302 between the sub 192 and the BHA 292. This transmission may be directed to a control unit within the BHA 292, as will be described below, or may be directed to a surface control unit via the BHA 292 as an intermediary device. Other embodiments may include other communication channels, mechanisms, and configurations, including wired communications between sensor controller 190 and BHA 292 and a direct communications pathway between the sensor controller 190 and a surface control unit.

As illustrated, the sensor controller 190 may transmit the measurements to a surface telemetry transceiver 362 using a long haul telemetry system 364 within the BHA 292. In particular, the sensor controller 190 may transmit the measurements to the BHA 292 via the short-hop telemetry channel 302, and the BHA 292 may communicate the measurements over a simplex (one direction, up in this case) or duplex (bi-directional) telemetry channel between the telemetry system 364 and the surface transceiver 362. The surface control unit 306 of FIG. 8 may receive the measurements from the surface transceiver 362. In other embodiments, the surface control unit 306 may receive the measurements from the sensor controller 190 or some other downhole control unit after those control units are removed to the surface. The surface control unit 306 may process the received measurements to determine one or more characteristics of the formation corresponding to the received measurements. In certain embodiments, the determined characteristics may be used in a drilling control program run at the surface control unit 306 to make a drilling decision, similar to the one described above, and generate a control signal corresponding to the drilling decision. If the decision is made while the BHA 292 is located downhole, the generated control signal may be transmitted through the telemetry channel 364 to a downhole steering controller 366 of the BHA 292.

As previously discussed, once the sensor controller 190 has received the look ahead measurements from the drill bit 10, the sensor controller 190 may store the received measurements, further process and then store the received measurements to determine a characteristic of a portion of the formation, and/or transmit the received or processed measurements to the above described surface control unit 306. In certain embodiments, the sensor controller 190 may determine the characteristic of the portion of the formation from the received measurements and then automatically make a drilling decision based on the determined characteristic and a decision algorithm stored as instructions in a memory device coupled to a processor of the sensor controller 190. For example, if the determined characteristic is the location of a strata boundary within the portion of the formation, the sensor controller 190 may output a control signal via the short hop telemetry module 302 to the motor downhole steering controller 366 that causes the motor or rotary steerable tool to alter the angle and direction of the drill bit 10. This may enable the wellbore to be steered in a more desirable direction based on the data received from the roller cone resistivity sensor, such as by steering the wellbore into a detected pay zone or maintaining the well bore position within a pay zone by maintaining a set distance from a bed boundary.

As described above, the associated electronics for the in-bit antenna loop 24 may be located outside of the drill bit, such as in an instrument sub, or in the drill bit. Locating the associated electronics outside of the drill bit may reduce the cost of the drill bit and allow for the associated electronics to be reused by a new bit after the an initial drill bit wears out during the drilling process. This is particularly beneficial because typical drilling operations wear out many drill bits. When the associated electronics are located outside of the drill bit, however, the new drill bit may need to be calibrated to the associated electronics to optimize the measurements taken by the in bit antenna receiver.

Having described the physical layout of the drilling system 270 with the antenna loop 24 disposed in a roller cone 14, a detailed description of the computations used in operation of the antenna sensor is provided below. A position of the one or more antennas 24 in the roller cone drill bit 10 can be described using the below parametric equation 1. Equation 1 is used to describe a circle in the x-y plane, where $\theta$ represents an angular position around the length of the antenna loop 24 and where $\rho$ represents a radius of the antenna loop 24.

$$f(\theta)=\rho\cos(\theta)\hat{x}+\rho\sin(\theta)\hat{y}+0\hat{z} \quad (1)$$

It may be desirable to describe an antenna loop 24 whose center is offset along any axis in three dimensions from a position at the center of the drill bit 10. For example, if the antenna loop 24 is positioned a radial distance from the central axis of the drill bit 10, this may be simulated via the center of the circle described in Equation 1 being offset along one of the x or y axes. In addition, if the antenna loop 24 is positioned above or below the drill bit, this may be simulated via the center of the circle being offset on the z-axis. It should be noted that positioning the antenna loop 24 below the drill bit 10 may not be acceptable in some embodiments. However, if used in the context of through-bit logging tools, the antenna loop 24 may be positioned below the drill bit 10 at least temporarily. Further, it should be noted that the coordinate system and axes could be positioned at any point along the length of the drill string. No matter where the relative positioning of the antenna loop 24 is relative to the chosen coordinate system, the equation representing the circle formed therein by the antenna loop 24 may be updated to reflect a shift along any of the axes. For example, in a given embodiment where the antenna loop 24 is offset from the z-axis by a distance l along the x-axis, the equation may be updated as follows.

$$f(\theta)=\rho(\cos(\theta)+l)\hat{x}+\sin(\theta)\hat{y}+0\hat{z} \quad (2)$$

In addition to positioning the center of the circle appropriately in the coordinate system, it may be desirable to provide an angular adjustment to the equation based on a relative angular position of the antenna loop 24 disposed on the roller cone 14. To accomplish this, the antenna equation can be rotated on the y-axis such that it is inclined at the same angle as the journal bearing 56, which is at a known angle α for a given drill bit 10. To rotate the antenna equation in this manner, the following rotation matrix may be applied for rotation about the y-axis, yielding equation 3 below. In the below equation, α represents the angle of the journal arm 56 from the central longitudinal axis of the drill bit 10, θ represents the angular position around the antenna loop 24, and ρ represents the radius of the antenna loop 24. Similar rotation matrices may be applied for rotations about the x-axis or z-axis.

$$f_1(\alpha, \theta) = \rho \begin{bmatrix} \cos(\alpha) & 0 & \sin(\alpha) \\ 0 & 1 & 0 \\ -\sin(\alpha) & 0 & \cos(\alpha) \end{bmatrix} * \begin{bmatrix} \cos(\theta) + l \\ \sin(\theta) \\ 0 \end{bmatrix} \begin{bmatrix} \hat{x} \\ \hat{y} \\ \hat{z} \end{bmatrix} = \quad (3)$$

$$\rho((\cos(\theta) + l) * \cos(\alpha)\hat{x} + \sin(\theta)\hat{y} - (\cos(\theta) + l) * \sin(\alpha)\hat{z})$$

In some embodiments, the drill bit 10 may include several antenna loops 24 disposed thereon. Indeed, any desirable number of antenna loops 24 may be disposed on a drill bit 10 having any number of roller cones 14. These antenna loops 24 may be modeled according to similar equations as those provided above. In some embodiments, multiple antenna loops 24 may be disposed about the drill bit 10 at positions that are related to each other. For example, the drill bit 10 may include three antennas 24, each antenna disposed on a respective roller cone 14 of a tri-cone bit. In addition, these antenna loops 24 may include the same radius and angle of the journal arm 56 relative to the drill bit longitudinal axis. It should be noted, however, that the following equations could be manipulated to support any radius and orientation of the antenna loops 24 should there be a lack of symmetry in the bit construction.

The expression provided in equation 3 may be translated into a simple parametric equation for plotting purposes. For example, the antenna loop 24 could be positioned in the x-z plane with the y-axis in the center of the loop. In this example, the angular position of the journal arm 56 and the antenna loop 24 is defined according to α=0.5π. To plot this antenna loop 24, the below parametric equation may be used.

$$x = \cos(\theta) * \cos(0.5\pi)$$

$$y = \sin(\theta)$$

$$z = -\cos(\theta) * \sin(0.5\pi) \quad (4)$$

For the above described tri-cone bit having three antenna loops 24 of the same approximate radius and angle from the bit axis, the two other antenna loops 24 may be rotated approximately 120 degrees apart from each other. To model these loops, two additional rotation matrices may be applied to rotate the above described circle into these other planes. These two other equations may be obtained by applying a z-axis rotation matrix to equation 3. In the following equation, β represents an angular position of the roller cone 14 about the z-axis of the drill bit 10.

$$f_2 = \quad (5)$$

$$R_z(\beta) * f_1(\alpha, \theta) = \rho \begin{bmatrix} \cos(\beta) & -\sin(\beta) & 0 \\ \sin(\beta) & \cos(\beta) & 0 \\ 0 & 0 & 1 \end{bmatrix} \begin{bmatrix} (\cos(\theta) + l)\cos(\alpha) \\ \sin(\theta) \\ -(\cos(\theta) + l)\sin(\alpha) \end{bmatrix} \begin{bmatrix} \hat{x} \\ \hat{y} \\ \hat{z} \end{bmatrix} =$$

$$\rho((\cos(\theta) + l)\cos(\alpha)\cos(\beta) - \sin(\theta)\sin(\beta))\hat{x} +$$
$$\rho((\cos(\theta) + l)\cos(\alpha)\sin(\beta) + \sin(\theta)\cos(\beta))\hat{y} - \rho(\cos(\theta) + l)\sin(\alpha)\hat{z}$$

Equation 5 is a generalized equation that can be used to model any antenna loop 24 having with an angular position of θ, a radius of ρ, an incline angle α of the roller cone 14 having the antenna loop 24 relative to the axis of the drill bit 10, and an angle β of the roller cone 14 positioned about the axis of the drill bit 10. Letting β equal whatever angular position the roller cone 14 is about the z-axis of the drill bit 10 may allow equation 5 to become a generalized expression for any antenna loop 24 placed on the roller cone 14 of the drill bit 10. Thus, a tri-cone bit may feature antenna loops 24 at the following angles.

$\beta_1 = 0° = 0$ radians $\beta_2 = 120° = 2/3\pi$ radians $\beta_3 = 240° = 4/3\pi$ radians Each angle β represents an angular position around the central axis of the drill bit 10 where the loop antenna 24 is positioned. These β values may be different for other embodiments of the roller cone drill bit 10. For example, if the bit 10 has 4 roller cones 14, each roller cone 14 including an antenna loop 24, the equations may include 4 β's positioned along the 360 degrees or 2π radians around the drill bit axis.

As discussed above, these equations represent a generalized set of Cartesian coordinates that can be used to model the position and orientation of the antenna loops 24 disposed on roller cones 14 of a roller cone drill bit 10 in accordance with the present techniques. These equations may form the basis for inductive coupling of an antenna configured to transmit electromagnetic energy into a well formation and an antenna configured to receive electromagnetic energy reflected back from the formation. Using these equations, it may be desirable to examine the differences of response from different receiver and transmitter antenna combinations, as discussed in detail below. For example, it may be desirable to compare the responses from any two receiver antennas using a single transmitter antenna, as well as responses from a single receiver antenna using two transmitter antennas, while the drill bit 10 is stationary and while the drill bit 10 is rotating in the wellbore.

The sensitivity of a given transceiver antenna at any given point in space may be defined as a relative contribution of the changes in conductivity of the given point compared to a total received signal. In general, an antenna may receive most of its signal from the associated sensitive volume. Thus, the sensitivity of a given point in space may be obtained by perturbing the conductivity of that particular point in space and recording the changes in the received signal. Specifically, the sensitivity of a given point in space may be represented by the following equation 6.

$$S(x, y, z) = \frac{(V(\sigma + \Delta\sigma(x, y, z)) - V(\sigma))}{\Delta\sigma} \quad (6)$$

In equation 6, S(x,y,z) represents the sensitivity of the antenna loop 24 at coordinates (x,y,z), V(σ) represents a voltage received for a conductivity distribution of σ, Δσ(x, y,z) represents a perturbation term which is a non-zero value only at point (x,y,z), and Δσ is the magnitude of the perturbation term. A 3-dimension (3D) sensitivity plot may be difficult to visualize, so a 2D sensitivity plot and corresponding 1D sensitivity plot are generally used to illustrate the sensitivity of the antenna loops. These plots may be provided according to the equations below.

$S(y,z)$=Integral of $S(x,y,z)$ along $x$ $S(x,z)$=Integral of $S(x,y,z)$ along $y$ $S(x,y)$=Integral of $S(x,y,z)$ along $z$ (7)

$S(x)$=Double-integral of $S(x,y,z)$ along $y$ and $z$ $S(y)$=Double-integral of $S(x,y,z)$ along $x$ and $z$ $S(z)$=Double-integral of $S(x,y,z)$ along $x$ and $y$ (8)

A sensitivity study has been performed to compare the sensitivity of several different locations of the antenna loops 24 disposed on a roller cone drill bit 10. The study focused generally on sensitivity of the antenna loops 24 to conductivity. However, the disclosed antenna loop system is also sensitive to dielectric constant of the medium, which can be used to solve for dielectric constant as well. It may also be possible to determine the sensitivity of the antenna loops 24 to conductivity and dielectric constant simultaneously, as performed in existing wireline dielectric tools.

Certain antenna loop positions were considered during the sensitivity study. Turning back to FIG. 1, the illustrated drill bits 10 feature antenna loops 24 disposed at certain positions that were considered in the study. More specifically, the drill bit 10 may include antenna loops 24 positioned at each of the following locations: A1, A2, B1, B2, and C. These locations are designated as follows in FIG. 1. A1 corresponds to one of several antenna loops 390 disposed in the 12A position of one of the roller cones 14. A2 corresponds to one of several antenna loops 392 disposed in the 12A position of another one of the roller cones 14. B1 corresponds to an antenna loop 394 disposed in one of the 12B positions between two roller cones 14. B2 corresponds to an antenna loop 396 disposed in another 12B position, this one located directly adjacent one of the roller cones 14. C corresponds to an antenna loop 398 disposed in the 12C position about the drill bit 10.

As illustrated, the 12A positioned antenna loops 390 and 392 may be positioned approximately 120 degrees from each other as measured about a z-axis 400 of the drill bit 10. The antenna loops 390 and 392 used in the sensitivity study may each have the same radius. In the illustrated embodiment, the 12B positioned antenna loops 394 and 396 may be approximately 90 degrees from each other as measured about the z-axis 400. Although these locations A1, A2, B1, B2, and C were used in the present study, other locations may be utilized and studied in a similar manner to determine an appropriate drill bit position for the transmitter and receiver antennas to perform a desired function.

Figure 10C:
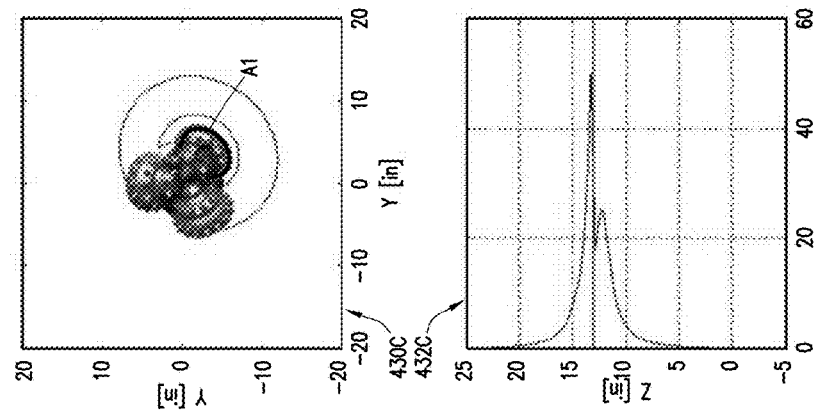
FIGS. 10A-10C are a series of plots illustrating sensitivity measurements of a roller cone drill bit having one receiver antenna, in accordance with an embodiment of the present disclosure.
Figure 10B:
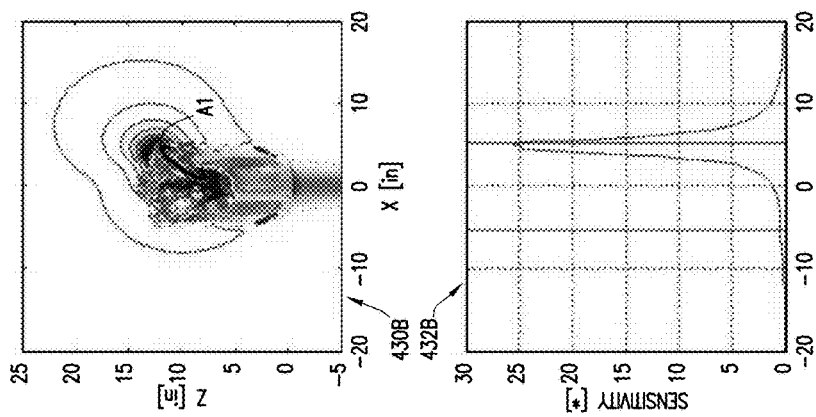
Figure 10A:
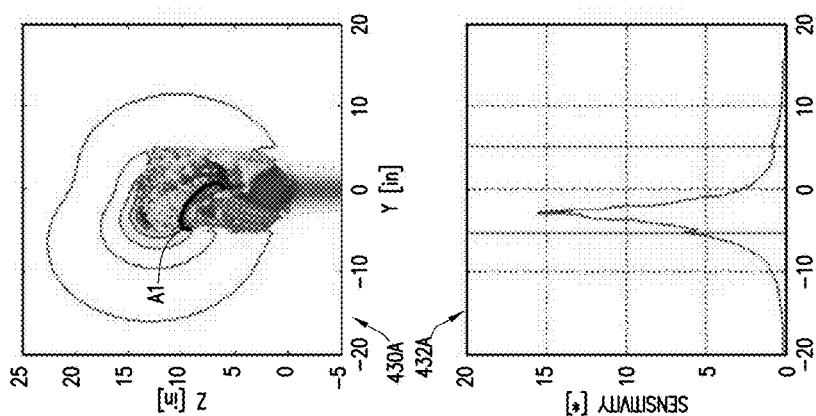
Figures 11A, 11B, 11C:
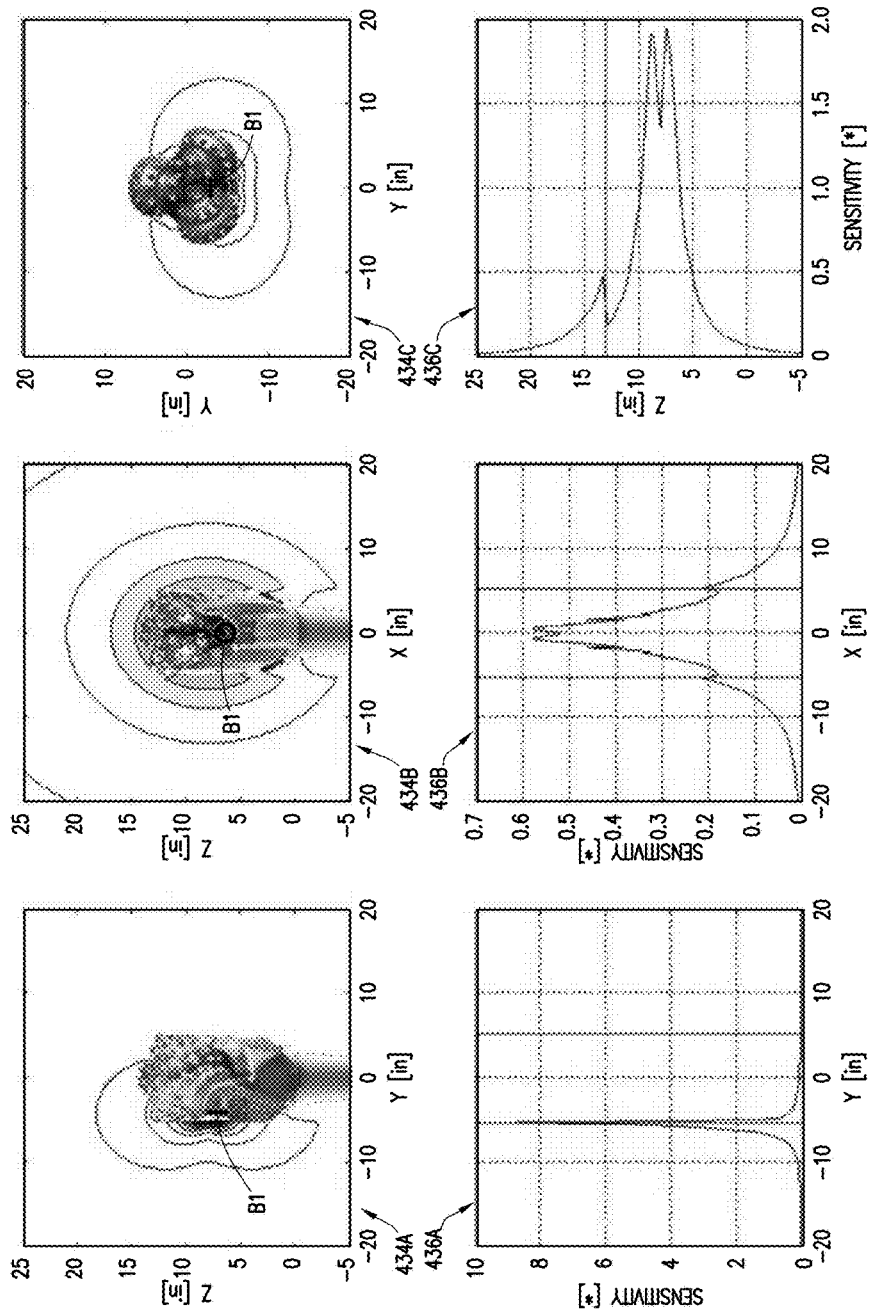
FIGS. 11A-11C are a series of plots illustrating sensitivity measurements of a roller cone drill bit having one receiver antenna, in accordance with an embodiment of the present disclosure.

FIG. 10 illustrates plots showing the 2D and 1D sensitivities of an antenna loop that is positioned as a receiver at the location A1, as measured during the sensitivity study. Similarly, FIG. 11 illustrates plots showing the 2D and 1D sensitivities of an antenna loop that is positioned as a receiver at the location B1. FIG. 12 illustrates plots showing the 2D and 1D sensitivities of an antenna loop that is positioned as a receiver at the location C. It should be noted that the antenna placements and bit orientation shown in these FIGS. 10-12 are approximate locations that are used for illustrative purposes only. In FIGS. 10-12, a single frequency excitation of 1 MHz is used to drive the antennas. The resistivity of the formation is assumed to be 10 Ωm.

FIG. 10 shows that both the radial sensitivity distribution and the axial sensitivity distribution of the transceiver antenna are contained within 1-2 inches of the antenna position. This is indicated by the dark portions in the 2D plots 430 being located relatively close to the drill bit 10, as well as the high sensitivity measurements shown in the corresponding 1D plots 432. In addition, the x-y sensitivity plot 430C and the x-z sensitivity plot 430B illustrate a higher sensitivity on one side of the drill bit, particularly the side in which the roller cone extends with the antenna. As a result, this location A1 exhibits a relatively high azimuthal sensitivity. This azimuthal sensitivity may be desirable in certain contexts where it is important to determine the resistivity on one side of the bit. The arrangement using a receiver antenna in the A1 position may be especially suitable for very shallow and azimuthal measurements of resistivity.

FIG. 11 shows that both the radial sensitivity distribution and the axial sensitivity distribution of the transceiver antenna are contained within about 1-2 inches of the antenna position, similar to FIG. 10. This is indicated by the dark portions in the 2D plots 434 being located relatively close to the drill bit 10, as well as the high sensitivity measurements shown in the corresponding 1D plots 436. However, due to the smaller antenna size of the antenna disposed in the B1 position, the sensitivity in the radial direction (i.e., about the z-axis of the bit) is generally shallower than the sensitivity from the A1 position.

FIG. 12 shows that both the radial sensitivity distribution and the axial sensitivity distribution of the transceiver antenna are contained within about 5 inches of the antenna position, much larger than in FIGS. 10 and 11. This is indicated by the dark portions in the 2D plots 438 extending further out from the drill bit 10, as well as the wider spaced sensitivity measurements shown in the corresponding 1D plots 440. In addition, the illustrated C placement of the antenna yields an azimuthally symmetric sensitivity distribution, as indicated in the x-y plane 2D plot 438C, meaning that the sensitivity distribution is generally the same in all directions around the z-axis of the drill bit. Thus, there is no azimuthal sensitivity for this particular antenna configuration. As a result, this C placement configuration may be more suitable for deeper and non-azimuthal sensing applications.

Figures 14A, 14B, 14C:
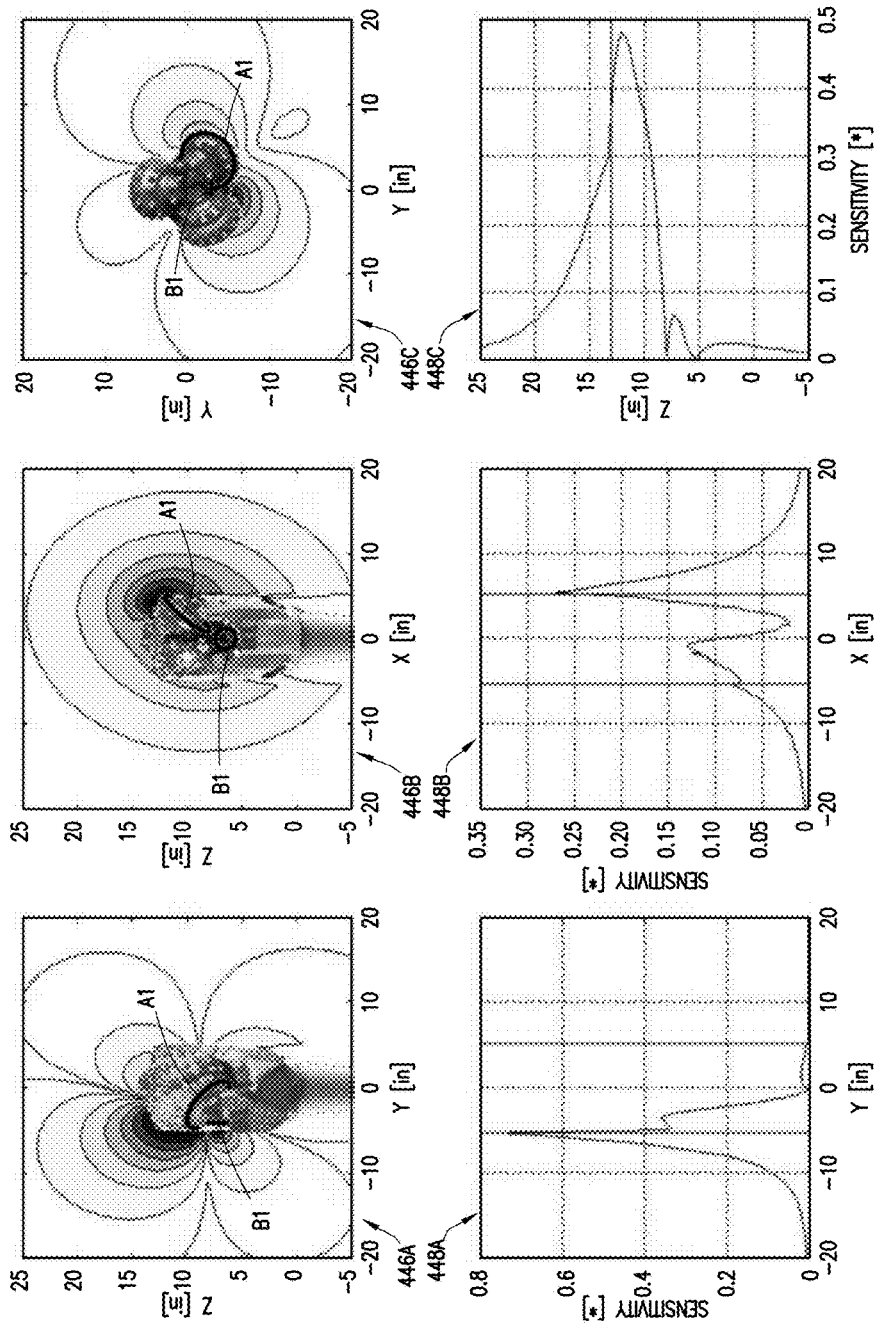
FIGS. 14A-14C are a series of plots illustrating sensitivity measurements of a roller cone drill bit having one transmitter antenna and one receiver antenna, in accordance with an embodiment of the present disclosure.

FIG. 13 illustrates plots showing the 2D and 1D sensitivities of a two antenna (transmitter-receiver) loop system where one antenna loop is positioned at the location A1 and the other antenna is positioned at the location A2, as measured during the sensitivity study. Similarly, FIG. 14 illustrates plots showing the 2D and 1D sensitivities of a two antenna (transmitter-receiver) loop system where one antenna loop is positioned at the location A1 and the other antenna is positioned at the location B1. FIG. 15 illustrates plots showing the 2D and 1D sensitivities of a two antenna (transmitter-receiver) loop system where one antenna loop is positioned at the location A1 and the other antenna is positioned at the location C. Further, FIG. 16 illustrates plots showing the 2D and 1D sensitivities of a two antenna (transmitter-receiver) loop system where one antenna loop is positioned at the location B1 and the other antenna is positioned at the location B2. Still further, FIG. 17 illustrates plots showing the 2D and 1D sensitivities of a two antenna (transmitter-receiver) loop system where one antenna loop is positioned at the location B1 and the other antenna is positioned at the location C. It should be noted that, due to electromagnetic reciprocity, the roles of transmitter and receiver may be interchangeable in each of these embodiments without affecting the illustrated sensitivity distribution. As before, the antenna placements and bit orientation shown in these FIGS. 13-17 are approximate locations that are used for illustrative purposes only.

FIG. 13 shows that the sensitivity of the A1-A2 configuration is focused sideways in a shape of two beams with a depth of investigation of around 2-3 inches. This is indicated by the dark portions in the 2D plots 442 being located generally close to the drill bit 10 on two sides, as well as the two-peak sensitivity measurements shown in the corresponding 1D plots 444. Due to the dual azimuthal sensitivity focus in the A1-A2 embodiment, this configuration may not be suitable for azimuthal resistivity measurements.

FIG. 14 shows that the sensitivity of the A1-B1 configuration is focused sideways in a shape of two beams with a depth of investigation of around 2-3 inches, similar to FIG. 13. This is indicated by the dark portions in the 2D plots 446 being located generally close to the drill bit 10 on two sides, as well as the two-peak sensitivity measurements shown in the corresponding 1D plots 448. However, the two beams are at different axial positions and have different strengths, as illustrated by the large-small peak combinations illustrated in the 1D plots 448 and the differing sizes and extensions of the dark portions in the y-z plane 2D plot 446A. This is in part due to the different respective sizes of the antennas disposed in the A1 and B1 locations, as well as due to the placements of these antennas at different distances from the z-axis of the bit. Again, due to the dual azimuthal sensitivity focus, this A1-B1 configuration may not be suitable for azimuthal interpretation.

FIG. 15 shows that the sensitivity of the A1-C configuration is relatively deep (5-10 inches) with some small azimuthal sensitivity. This is indicated by the dark portions in the 2D plots 450 extending relatively far out from the drill bit 10 on different sides, the dark portions extending to a greater depth on one side of the bit than on the other. This configuration may be suitable for making stable resistivity measurements beyond the mud column (e.g., into the formation beyond where the mud being pumped through the drill bit reaches). However, resolution of the axial sensitivity measurements is generally limited in the A1-C configuration.

FIG. 16 shows that the sensitivity of the B1-B2 configuration is focused in a shape of three azimuthal beams with a depth of investigation of only around 1-2 inches. This is indicated by the dark portions in the 2D plots 454 being located relatively close to the drill bit 10 on three sides, as well as the multi-peak sensitivity measurements shown in the corresponding 1D plots 456. This configuration may be suitable for taking shallow azimuthal readings, although the azimuthal resolution may be lower due to the three focus beams that cover an angle of approximately 120 degrees.

FIG. 17 shows that the sensitivity distribution of the B1-C configuration is approximately 1-2 inches deep. This is indicated by the dark portions in the 2D plots 458 being located generally close to the drill bit 10, as well as the high peak sensitivity measurements shown in the corresponding 1D plots 460. This configuration shows the strongest azimuthal sensitivity among the other configurations, as indicated by the high sensitivity focused on one side of the drill bit shown in the x-y plane 2D plot 458C and the y-axis 1D plot 460A. Thus, the B1-C configuration may be particularly suitable for use where azimuthal sensitivity is more important than depth of investigation.

As illustrated in the plots of FIGS. 10-17, there is often a trade-off between depth of field and resolution of the measurements that can be performed via the antennas disposed in the roller cone drill bit 10. For example, the A1 sensor arrangement described above with reference to FIG. 10 has relatively high levels of sensitivity within relatively small distances from the drill bit. Thus, this sensor placement may yield resistivity measurements with very high resolution and with a low depth of field. In contrast, the A1-C sensor arrangement described above with reference to FIG. 15 has relatively low levels of sensitivity within relatively large distances from the drill bit. Thus, this sensor placement may yield resistivity measurements over a large depth of field but with relatively low resolution. Depending on the type of formation and desired measurements to be collected, a drill bit with a suitable antenna arrangement may be selected for the job.

Table 1 shown below lists the direct signal levels from the transmitter to the receiver measured for the configurations of FIGS. 13-17. These signal levels were determined for a single turn antenna with 1 Amp excitation, and a spacing of 0.1 inch between the antenna and the ferrite backing 114 (as discussed above with reference to FIG. 4). It should be noted that all the voltages listed in table 1 are large enough for detection and measurement using standard measurement systems, which are typically sensitive up to approximately 10 nV.

TABLE 1

| | Configuration | | | | |
|---|---|---|---|---|---|
| | A1-A2 | A1-B1 | A1-C | B1-B2 | B1-C |
| Voltage Magnitude | 180.21 µV | 13.71 µV | 32.63 µV | 45.10 µV | 42.18 µV |

The antenna loops described above can be driven by a voltage-controlled or current-controlled circuit. In some embodiments, the control circuit may use a single-frequency, multi-frequency, or pulsed excitation with an arbitrary transient shape signal to drive the antennas. Measurements can be made as a function of time or a function of frequency. In the case of time measurement, induced voltages or induced currents on the receiving antenna (or transceiver) can be recorded. The phase of the received signal can be referenced to the transmitter or any other arbitrary clock. In cases where no phase synchronization is available, only amplitude data can be used for interpretation. The interpretation can be performed by comparing the received signals to those in an interpretation table. In some embodiments, the interpretation table may be constructed by modeling the antennas or doing experiments in a laboratory setting.

In the case of a time measurement, an interpretation table may be constructed as set forth below in equation 9. In this equation, $R_i$ represents the i'th resistivity and $V_i(t_1)$ represents the i'th voltage corresponding to time $t_1$. The time of measurement may be chosen based on the desired depth of investigation. That is, in the case of shallow measurements, the chosen time may be small. In the case of deep measurements, the chosen time may be larger.

$$R_i \rightarrow V_i(t_1) \quad (9)$$

In the case of a frequency measurement, the interpretation table may be constructed as set forth below in equations 10-12. In equation 10, $C_i(f_1)$ is the i'th complex current or voltage measurement corresponding to the frequency $f_1$. $A_i(f_1)$ is the i'th current or voltage amplitude measurement corresponding to the frequency $f_1$. $P_i(f_1)$ is the i'th current or voltage phase measurement corresponding to the frequency $f_1$. The frequency of measurement can be chosen based on the desired depth of investigation. That is, in the case of shallow measurements, the chosen frequency may be large. In the case of deep measurements, the chosen frequency may be smaller. An example range of frequency that may be utilized for the measurements includes 100 kHz-10 GHz. Signal level is proportional to the square of the frequency in cases where the current is kept constant. Attenuation of the signal may increase exponentially with the frequency. As a result, for a given resistivity measurement, there may be an optimum operating frequency.

$$R_i = C_i(f_1) \tag{10}$$

$$R_i = A_i(f_1) \tag{11}$$

$$R_i = P_i(f_1) \tag{12}$$

The interpretation tables described above may be calculated experimentally by placing the roller cone drill bit in tanks filled with water of different salinity. A resistivity measurement, $R_i$, can then be made for each salinity value using a separate fluid resistivity measurement device. Corresponding measurements, $V_i(t_1)$, $C_i(f_1)$, $A_i(f_1)$, and $P_i(f_1)$ can then be taken and stored in a table. This table may later be used to back-calculate for $R_i$ using any of the above-described measurement values. This calculation is generally referred to the inverse solution.

In some embodiments, an iterative scheme can be used instead of the inverse solution in order to calibrate and interpret the resistivity measurements. In the iterative scheme, at each iteration a better estimate of $R_i$ is obtained as a result of a walk in the input measurement space. The iterations may be terminated when a mismatch between the measurement and the modeled measurement reaches a desired lower threshold.

Embodiments disclosed herein include:

A. A system including a roller cone drill bit for drilling a wellbore through a subterranean formation. The roller cone drill bit includes a journal arm, a roller cone rotatably coupled to the journal arm, and a first antenna loop disposed in the roller cone to detect magnetic energy or electromagnetic energy indicative of a target, a resistivity, or a boundary of the subterranean formation or a man-made structure or object in the subterranean formation.

B. A drilling system including a roller cone drill bit including a roller cone and at least one antenna loop disposed in the roller cone for detecting magnetic energy or electromagnetic energy from a subterranean formation or man-made structure or object. The drilling system also includes a sensor controller disposed outside of the roller cone drill bit and communicatively coupled to the at least one antenna loop to receive a signal from the at least one antenna loop indicative of the detected magnetic or electromagnetic energy.

C. A method including rotating a roller cone of a roller cone drill bit to drill into a subterranean formation. The method also includes receiving at least a portion of magnetic energy or electromagnetic energy emanating from the subterranean formation or a man-made structure or object, via a first antenna loop disposed in the roller cone.

Each of the embodiments A, B, and C may have one or more of the following additional elements in combination:

Element 1: further including a second antenna loop disposed in the roller cone drill bit to function as a transmitter or a receiver for the first antenna loop. Element 2: wherein the roller cone drill bit further includes a bit shank disposed around the journal arm, wherein the second antenna loop is disposed on the bit shank. Element 3: wherein the roller cone drill bit further includes a body for coupling the roller cone drill bit to another drilling component, wherein the second antenna loop is disposed around a circumference of the body. Element 4: wherein the first antenna loop forms a circumferential path around a face of the roller cone. Element 5: wherein the first antenna loop cuts across a diameter of the roller cone in a shape that generally tracks an outer face of the roller cone and loops along a circumferential path around an opposing face of the roller cone. Element 6: wherein the roller cone drill bit further includes a slip ring assembly disposed between the roller cone and the journal arm, and a pair of wires electrically coupled between opposing ends of the first antenna and the slip ring assembly. Element 7: wherein the roller cone drill bit further includes an electronics assembly disposed in the roller cone drill bit for receiving and processing a signal output via the first antenna. Element 8: wherein the electronics assembly is disposed in the journal arm. Element 9: wherein the roller cone drill bit further includes a pressure balance channel disposed through the journal arm and a cable routed through the pressure balance channel to carry a signal indicative of the target, resistivity, or boundary of the subterranean formation or man-made structure or object through the roller cone drill bit. Element 10: wherein the roller cone drill bit further includes a focusing element and a ferrite component disposed around the first antenna loop in the roller cone. Element 11: wherein the roller cone drill bit comprises three roller cones and wherein the first antenna is disposed in one of the three roller cones.

Element 12: further including an instrument sub coupled to the roller cone drill bit, wherein the sensor controller is disposed in the instrument sub. Element 13: further including a short-hop telemetry system coupling the instrument sub to a bottom hole assembly (BHA) module disposed above the instrument sub. Element 14: further including a downhole steering controller communicatively coupled to the sensor controller to adjust a steering of the drilling system based on the signal received from the at least one antenna loop. Element 15: wherein the roller cone drill bit further includes an electronics assembly for filtering and/or digitizing the signal from the at least one antenna loop before the signal reaches the sensor controller.

Element 16: further including transmitting electromagnetic energy into the subterranean formation via a second antenna loop. Element 17: further including outputting a signal indicative of the intercepted magnetic or electromagnetic energy; receiving the signal via a sensor controller; and determining a resistivity of a portion of the subterranean formation and outputting a control signal based on the determined resistivity via the sensor controller.

Although the present disclosure and its advantages have been described in detail, it should be understood that various changes, substitutions and alterations can be made herein without departing from the spirit and scope of the disclosure as defined by the following claims.

What is claimed is:

1. A system, comprising:
a roller cone drill bit for drilling a wellbore through a subterranean formation, wherein the roller cone drill bit comprises:

a journal arm;
a roller cone rotatably coupled to the journal arm;
a transmitter antenna loop disposed in the roller cone drill bit, wherein the transmitter antenna loop outputs an electromagnetic signal into the subterranean formation; and
a receiver antenna loop disposed in the roller cone, wherein the receiver antenna loop detects magnetic energy or electromagnetic energy emanating from the subterranean formation or from an object that is separate from the roller cone drill bit and located within the subterranean formation, in response to the electromagnetic signal transmitted into the subterranean formation.

2. The system of claim 1, wherein the roller cone drill bit further comprises a bit shank disposed around the journal arm, wherein the transmitter antenna loop is disposed on the bit shank.

3. The system of claim 1, wherein the roller cone drill bit further comprises a body for coupling the roller cone drill bit to another drilling component, wherein the transmitter antenna loop is disposed around a circumference of the body.

4. The system of claim 1, wherein the receiver antenna loop forms a circumferential path around a face of the roller cone.

5. The system of claim 1, wherein the roller cone comprises a cone-shaped outer face configured to cut into a bottom of the wellbore, wherein the receiver antenna loop traces a path across a diameter of the roller cone in a shape that generally tracks the cone-shaped outer face of the roller cone and loops along a circumferential path around a flat face of the roller cone on an opposite side of the roller cone from the outer face.

6. The system of claim 1, wherein the roller cone drill bit further comprises a slip ring assembly disposed between the roller cone and the journal arm, and a pair of wires that electrically couple opposing ends of the receiver antenna loop to the slip ring assembly.

7. The system of claim 1, wherein the roller cone drill bit further comprises an electronics assembly disposed in the roller cone drill bit and communicatively coupled to the receiver antenna loop for receiving and processing a signal output via the receiver antenna loop.

8. The system of claim 7, wherein the electronics assembly is disposed in the journal arm.

9. The system of claim 1, wherein the roller cone drill bit further comprises a pressure balance channel disposed through the journal arm and one or more wires routed through the pressure balance channel, wherein the one or more wires carry a signal indicative of the magnetic energy or electromagnetic energy detected by the receiver antenna loop to an electronics assembly located above the roller cone drill bit.

10. The system of claim 1, wherein:
the receiver antenna loop is located proximate an external edge of the roller cone; and
the roller cone drill bit further comprises:
a focusing element disposed about the receiver antenna loop, wherein the focusing element is located between the receiver antenna loop and the external edge of the roller cone; and
a ferrite component disposed in front of the receiver antenna loop in the roller cone on an opposite side of the receiver antenna loop from the focusing element.

11. The system of claim 1, wherein the roller cone drill bit comprises three roller cones and wherein the receiver antenna loop is disposed in one of the three roller cones.

12. The system of claim 1, wherein the roller cone drill bit further comprises at least a second roller cone, wherein the transmitter antenna loop is disposed in the second roller cone that is different from the roller cone in which the receiver antenna loop is disposed.

13. The system of claim 1, wherein the receiver antenna loop detects at least a portion of the electromagnetic signal that is reflected back as the magnetic energy or electromagnetic energy from the subterranean formation or from an object that is separate from the roller cone drill bit and located within the subterranean formation.

14. A drilling system, comprising:
a roller cone drill bit comprising:
a roller cone;
a transmitter antenna loop disposed in the roller cone drill bit, wherein the transmitter antenna loop outputs an electromagnetic signal into the subterranean formation; and
a receiver antenna loop disposed in the roller cone and positioned to detect magnetic energy or electromagnetic energy emanating from the subterranean formation or from an object that is separate from the roller cone drill bit and located within the subterranean formation, in response to the electromagnetic signal transmitted into the subterranean formation; and
a sensor controller disposed outside of the roller cone drill bit and communicatively coupled to the receiver antenna loop to receive a signal from the receiver antenna loop indicative of the magnetic or electromagnetic energy detected by the receiver antenna loop.

15. The drilling system of claim 14, further comprising an instrument sub coupled to the roller cone drill bit, wherein the sensor controller is disposed in the instrument sub.

16. The drilling system of claim 15, further comprising a short-hop telemetry system coupling the instrument sub to a bottom hole assembly (BHA) module disposed above the instrument sub.

17. The drilling system of claim 14, further comprising a downhole steering controller communicatively coupled to the sensor controller to adjust a steering of the drilling system based on the signal received from the receiver antenna loop.

18. The drilling system of claim 14, wherein the roller cone drill bit further comprises an electronics assembly disposed therein for filtering or digitizing the signal from the receiver antenna loop before the signal reaches the sensor controller.

19. A method, comprising:
rotating a roller cone of a roller cone drill bit to drill into a subterranean formation;
transmitting an electromagnetic signal from a first antenna loop into the subterranean formation; and
receiving, via a second antenna loop disposed in the roller cone, magnetic energy or electromagnetic energy emanating from the subterranean formation or from an object that is separate from the roller cone drill bit and located within the subterranean formation, in response to the electromagnetic signal transmitted into the subterranean formation.

20. The method of claim 19, further comprising:
outputting from the second antenna loop a signal indicative of the intercepted magnetic or electromagnetic energy;

receiving the signal via a sensor controller;
determining a resistivity of a portion of the subterranean formation via the sensor controller; and
outputting a control signal based on the determined resistivity via the sensor controller.

\* \* \* \* \*